United States Patent [19]

Spencer et al.

[11] Patent Number: 5,668,007
[45] Date of Patent: Sep. 16, 1997

[54] RECOMBINANT 21 KD COCOA PROTEIN AND PRECURSOR

[75] Inventors: Margaret Elizabeth Spencer, Sheffield; Rachel Hodge, Leicester, both of England

[73] Assignee: Mars UK Limited, Berkshire, England

[21] Appl. No.: 949,812

[22] PCT Filed: Jun. 7, 1991

[86] PCT No.: PCT/GB91/00913

§ 371 Date: Jan. 27, 1993

§ 102(e) Date: Dec. 11, 1992

[87] PCT Pub. No.: WO91/19800

PCT Pub. Date: Dec. 26, 1991

[30] Foreign Application Priority Data

Jun. 11, 1990 [GB] United Kingdom ............... 9013017

[51] Int. Cl.⁶ ............... C07K 14/415; C12N 15/29; C12N 1/21; C12N 1/19
[52] U.S. Cl. ............... 435/252.3; 530/370; 530/377; 530/379; 435/69.1; 435/71.1; 435/71.2; 435/172.3; 435/325; 435/252.33; 435/254.21; 435/320.1; 536/23.6; 536/23.1
[58] Field of Search ............... 530/370, 377, 530/329; 435/69.1, 71.1, 71.2, 72.3, 240.2, 252.3, 252.33, 254.21, 320.1; 536/23.6, 23.1

[56] References Cited

PUBLICATIONS

Biehl et al., J. Sci. Food Agric. 33, 1291–1304 (1982).
Fritz et al., Journal of Food Science 50, 946–950 (1985).
Pettipher, Café Cacao Thé, vol. XXXIV, No. 1, 23–26 (1990).
Wilson et al., Abstr. Pap. Am. Chem. Soc., #148 (1984).
Leah et al., Plant Molecular Biology 12, 673–682 (1989).
Spencer et al., Planta 183, 528–535 (1991).
M. P. Deutscher "Guide to Protein Purification" Meth. in Enzymology, vol. 182 pp. 602–613 738–751 (1990).
D.C. Wright et al. "Accumulation of Lipids, Proteins, Alkaloids . . ." J. Am. Oil Chemists Soc. 59(11) 475–479 (Nov. 1982).
P. J. Fritz et al. "Cocoa Butter Biosynthesis" J. Biol Chem. 261(1) 194–199 (Jan. 1986).
S. L. Berger et al. "Guide to Molecular Cloning Techniques" Meth. in Enzymology vol. 152: 393–399, 415–423, 432–447, 661–704 (1987).

Primary Examiner—Charles L. Patterson, Jr.
Assistant Examiner—Rebecca Prouty
Attorney, Agent, or Firm—Curtis, Morris & Safford

[57] ABSTRACT

A 21 kD protein, and its 23 kD expression precursor, as the source of peptide flavor precursors in cocoa (*Theobroma cacao*) have been identified. Genes coding for them have been probed, identified and sequenced, and recombinant proteins have been synthesized.

13 Claims, 10 Drawing Sheets

```
                                    M   K   T   A   T   A   V   V   L   L   L   F   A   F
CAGCAACATTTCACTTAACCATGAAGACCGCAACAGCCGTAGTTTTACTCCTCTTCGCCT
                    10          20          30          40          50          60

T   S   K   S   Y   F   F   G   V   A   N   A  A   N   S   P   V   L   D   T
TCACATCAAAATCATATTTCTTTGGGGTAGC-AACGCTGCAAACTCTCCTGTCTTGACA
        70          80          90         100         110         120

D   G   D   E   L   Q   T   G   V   Q   Y   Y   V   L   S   S   I   S   G   A
CTGATGGTGATGAGCTCCAAACTGGGGTTCAATATTACGTTCTTGTCATCGATATCGGGGTG
        130         140         150         160         170         180

G   G   G   L   A   L   G   R   A   T   G   Q   S   C   P   E   I   V   V
CTGGGGTGGAGGGCTAGCCCTAGGAAGGGCTACAGGTCAAAGCTGCCCAGAAATTGTTG
        190         200         210         220         230         240

Q   R   R   S   D   L   D   N   G   T   P   V   I   F   S   N   A   D   S   K
TCCAAAGACGATCCGACCTTGACAATGGTACTCCTGTAATCTTTTCAAATGCGGATAGCA
        250         260         270         280         290         300

D   D   V   R   V   S   T   D   V   N   I   E   F   V   P   I   R   D   R
AAGATGATGTTTGTCCGCGTATCTACTGATGTAAACATAGAGTTCGTTCCCATCAGAGACA
        310         320         330         340         350         360

L   C   S   T   S   T   V   W   R   L   D   N   Y   D   N   S   A   G   K   W
GACTCTGCTCAACGTTCAACTGTGTGGAGGCTTGACAATTATGACAATTCGGCAGGCAAAT
        370         380         390         400         410         420
```

FIG. 2A

```
    W   V   T   T   D   G   V   K   G   E   P   G   P   N   T   L   C   S   W   F
GGTGGGTGACAACTGATGGGGGTTAAAGGTGAACCTGGTCCTAACACTTTGTGCAGTTGGT
         430                 440                 450                 460                 470                 480

K   I   E   K   A   G   V   L   G   Y   K   F   R   F   C   P   S   V   C   D
TTAAGATTGAGAAGGCCGGAGTACTCGGTTACAAATTCAGGTTCTGTTCCTTCTCTGTG
         490                 500                 510                 520                 530                 540

S   C   T   L   C   S   D   I   G   R   H   S   D   D   D   G   Q   I   R
ATTCGTGCACAACTTTATGCAGCGATATTGGAAGACATTCAGATGATGATGGACAAATAC
         550                 560                 570                 580                 590                 600

L   A   L   S   D   N   E   W   M   F   K   K   A   S   K   T   I   K
GTTGGCTCTCAGTGACAATGAATGGGCATGGATGTTTAAGAAAGCAATAAGACAATAA
         610                 620                 630                 640                 650                 660

Q   V   V   N   A   N   D   *
AACAAGTTGTTAACGCGAACGATTAATTTAAGTTTAATGTACGAAGTGTACGTCCAAAG
         670                 680                 690                 700                 710                 720

CAGCAATACTAGCCCGGTCGTTACTTTCCCACTA[AATAAA]AGTTAAGTATGTGGTTCCCAGC
         730                 740                 750                 760                 770                 780

CCAGTGTTGTAATGCTATGCCTATGTAGTCAGTGTCTTGTTTGAGGGTGGAGATGCTTAA
         790                 800                 810                 820                 830                 840

AGGGTGTCTTCACAGTCCCAGCTTCGTAGTCTTTCAGCTTTATG[AATAAA]TGATTTGC
         850                 860                 870                 880                 890                 900

CTCTTGCCCTCTTTATT
         910
```

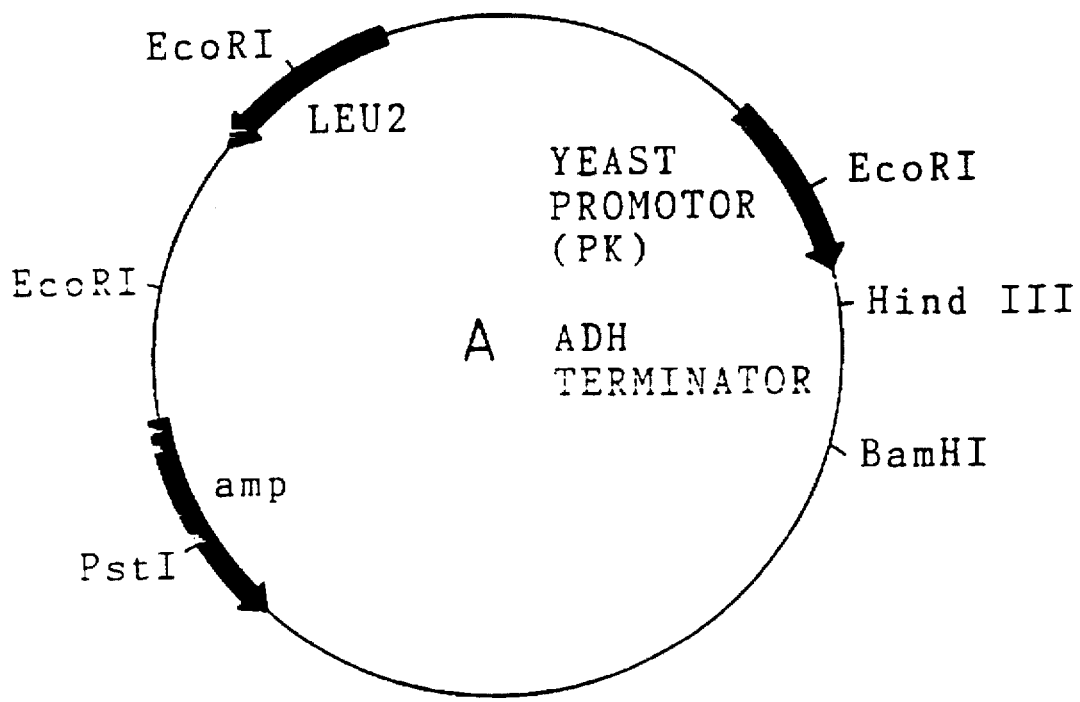
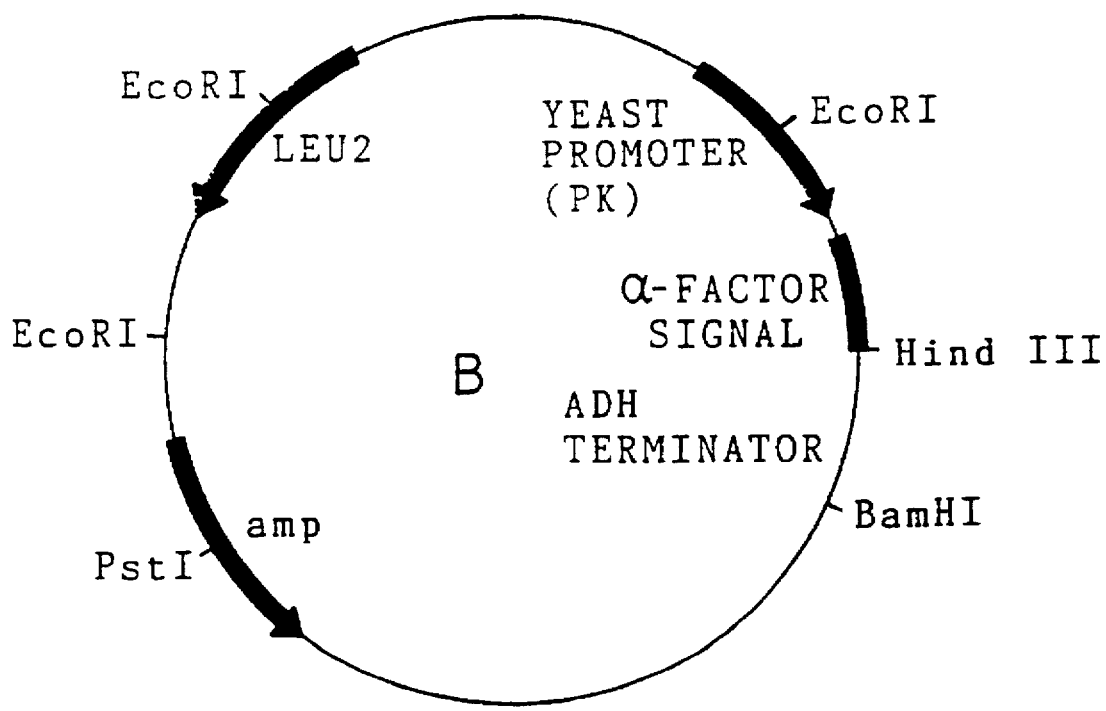
FIG. 5

FIG. 6A

YEAST PYRUVATE
KINASE GENE

```
                                                    MetSerArg
TTTACAAGACACCAATCAAAACAAATAAAACATCATCACAATGTCTAGA
```

↓

SEQUENCE ALTERED
TO CREATE CLONING
SITE

```
                                                    MetSerArg
TTTACAAGCTTCCAATCAAAACAAATAAAACATCATCACAATGTCTAGA
       ‾‾‾‾‾‾
         Hin
```

+

HIN-NCO LINKERS

```
AGCTTCCAATCAAAACAAATAAAACATCATCAC
  AGGTTAGTTTTGTTTATTTTGTAGTAGTGGTAC
```

↓

21kD EXPRESSION
VECTOR A

```
                                                          MetGluThr
TTTACAAGCTTCCAATCAAAACAAATAAAACATCATCACCATGGAGACC
       ‾‾‾‾‾‾                            ‾‾‾‾‾‾
         Hin                                Nco
```

FIG. 6B

YEAST ALPHA-FACTOR SIGNAL SEQUENCE

```
     1                            231
Met----GluGlyValSerLeuAspLysArgGlu
ATG----GAAGGGGTAAGCTTGGATAAAAGAGAG
                  Hin
```

HIN-NCO LINKERS

```
AGCTTGGATAAAAGAGC
    ACCTATTTTCTCGGTAC
```

IN-PHASE FUSION OF 21KD CODING REGION

```
Met----GluGlyValSerLeuAspLysArgAlaMetAlaAsn
ATG----GAAGGGGTAAGCTTGGATAAAAGAGCCATGGCAAAC
                  Hin              Nco
```

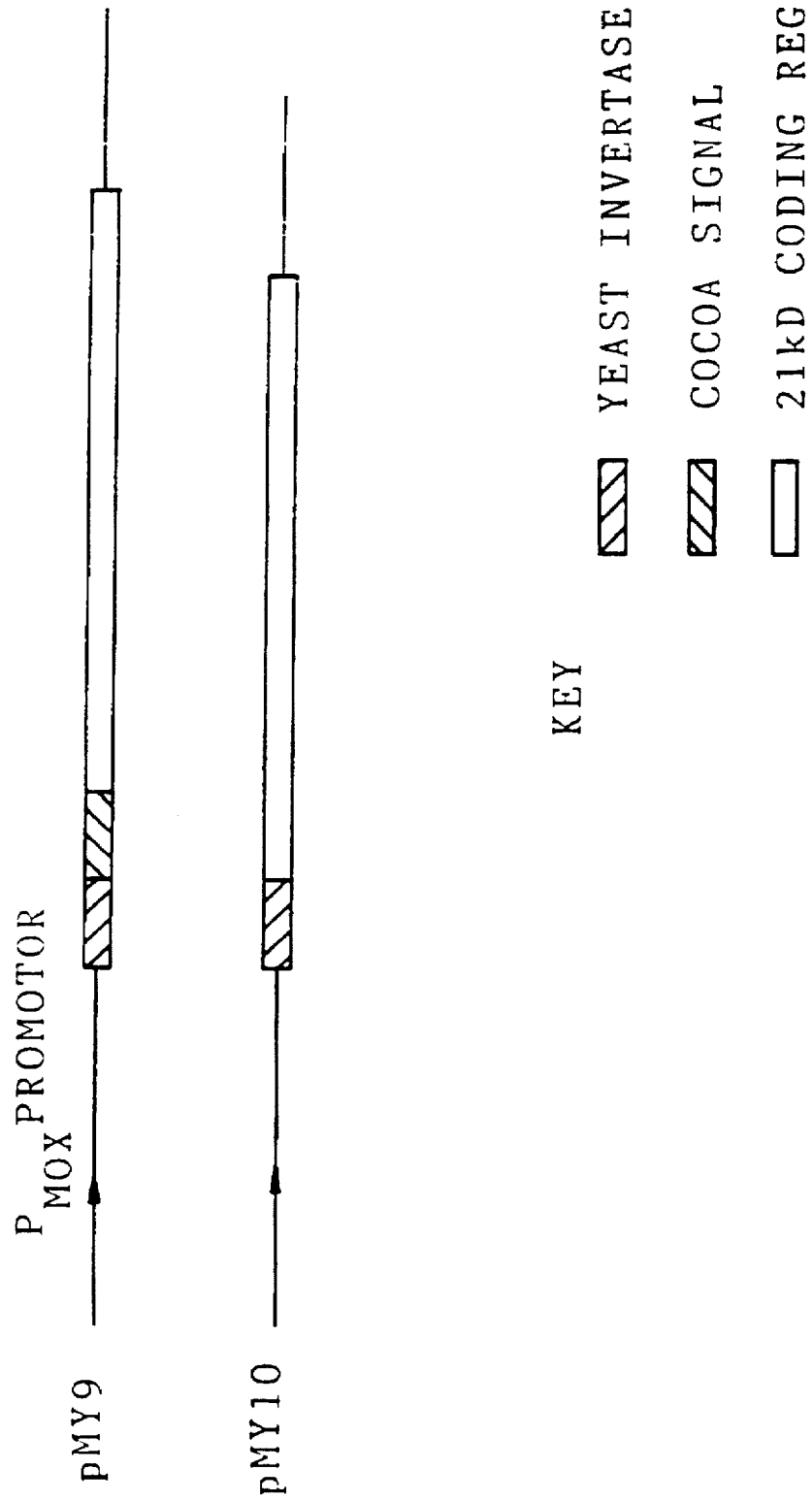

SEQUENCE LISTING ( 1 ) GENERAL INFORMATION:

( i i i ) NUMBER OF SEQUENCES: 28

( 2 ) INFORMATION FOR SEQ ID NO: 1:

( i ) SEQUENCE CHARACTERISTICS:
        ( A ) LENGTH: 917 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 21..686
        ( D ) OTHER INFORMATION: /product="DNA CODING SEQUENCE FOR 21kD PROTEIN AND DEDUCED AMINO ACIDS"

( x i ) SEQUENCE DESCRIPTION: SEQ ID NO: 1:

```
CAGCAACATT  TCACTTAACC  ATG  AAG  ACC  GCA  ACA  GCC  GTA  GTT  TTA  CTC                 50
                        Met  Lys  Thr  Ala  Thr  Ala  Val  Val  Leu  Leu
                         1                  5                        10

CTC  TTC  GCC  TTC  ACA  TCA  AAA  TCA  TAT  TTC  TTT  GGG  GTA  GCN  AAC  GCT             98
Leu  Phe  Ala  Phe  Thr  Ser  Lys  Ser  Tyr  Phe  Phe  Gly  Val  Ala  Asn  Ala
                     15                       20                      25

GCA  AAC  TCT  CCT  GTG  CTT  GAC  ACT  GAT  GGT  GAT  GAG  CTC  CAA  ACT  GGG            146
Ala  Asn  Ser  Pro  Val  Leu  Asp  Thr  Asp  Gly  Asp  Glu  Leu  Gln  Thr  Gly
               30                       35                       40

GTT  CAA  TAT  TAC  GTC  TTG  TCA  TCG  ATA  TCG  GGT  GCT  GGG  GGT  GGA  GGG            194
Val  Gln  Tyr  Tyr  Val  Leu  Ser  Ser  Ile  Ser  Gly  Ala  Gly  Gly  Gly  Gly
          45                       50                       55

CTA  GCC  CTA  GGA  AGG  GCT  ACA  GGT  CAA  AGC  TGC  CCA  GAA  ATT  GTT  GTC            242
Leu  Ala  Leu  Gly  Arg  Ala  Thr  Gly  Gln  Ser  Cys  Pro  Glu  Ile  Val  Val
     60                       65                       70

CAA  AGA  CGA  TCC  GAC  CTT  GAC  AAT  GGT  ACT  CCT  GTA  ATC  TTT  TCA  AAT            290
Gln  Arg  Arg  Ser  Asp  Leu  Asp  Asn  Gly  Thr  Pro  Val  Ile  Phe  Ser  Asn
75                       80                       85                       90

GCG  GAT  AGC  AAA  GAT  GAT  GTT  GTC  CGC  GTA  TCT  ACT  GAT  GTA  AAC  ATA            338
Ala  Asp  Ser  Lys  Asp  Asp  Val  Val  Arg  Val  Ser  Thr  Asp  Val  Asn  Ile
                    95                      100                     105

GAG  TTC  GTT  CCC  ATC  AGA  GAC  AGA  CTC  TGC  TCA  ACG  TCA  ACT  GTG  TGG            386
Glu  Phe  Val  Pro  Ile  Arg  Asp  Arg  Leu  Cys  Ser  Thr  Ser  Thr  Val  Trp
               110                      115                     120

AGG  CTT  GAC  AAT  TAT  GAC  AAC  TCG  GCA  GGC  AAA  TGG  TGG  GTG  ACA  ACT            434
Arg  Leu  Asp  Asn  Tyr  Asp  Asn  Ser  Ala  Gly  Lys  Trp  Trp  Val  Thr  Thr
          125                     130                     135

GAT  GGG  GTT  AAA  GGT  GAA  CCT  GGT  CCT  AAC  ACT  TTG  TGC  AGT  TGG  TTT            482
Asp  Gly  Val  Lys  Gly  Glu  Pro  Gly  Pro  Asn  Thr  Leu  Cys  Ser  Trp  Phe
     140                     145                     150

AAG  ATT  GAG  AAG  GCC  GGA  GTA  CTC  GGT  TAC  AAA  TTC  AGG  TTC  TGT  CCT            530
Lys  Ile  Glu  Lys  Ala  Gly  Val  Leu  Gly  Tyr  Lys  Phe  Arg  Phe  Cys  Pro
```

| | | | | | | | | | | | | | | | | |
|---|---|---|---|---|---|---|---|---|---|---|---|---|---|---|---|---|
|155| | | | |160| | | | |165| | | | |170| |
|TCT|GTC|TGT|GAT|TCG|TGC|ACA|ACT|TTA|TGC|AGC|GAT|ATT|GGA|AGA|CAT|578|
|Ser|Val|Cys|Asp|Ser<br>175|Cys|Thr|Thr|Leu|Cys<br>180|Ser|Asp|Ile|Gly|Arg<br>185|His| |
|TCA|GAT|GAT|GAT|GGA|CAA|ATA|CGT|TTG|GCT|CTC|AGT|GAC|AAT|GAA|TGG|626|
|Ser|Asp|Asp|Asp<br>190|Gly|Gln|Ile|Arg|Leu<br>195|Ala|Leu|Ser|Asp|Asn<br>200|Glu|Trp| |
|GCA|TGG|ATG|TTT|AAG|AAA|GCA|AGT|AAG|ACA|ATA|AAA|CAA|GTT|GTT|AAC|674|
|Ala|Trp|Met<br>205|Phe|Lys|Lys|Ala|Ser<br>210|Lys|Thr|Ile|Lys|Gln<br>215|Val|Val|Asn| |
|GCG|AAC|GAT|TAATTTAAG|TTTAATGTAC|GAAGTGTACG|TCCAAAGCAG| | | | | | | | | |723|
|Ala|Asn|Asp<br>220| | | | | | | | | | | | | | |

```
CAATACTAGC CGGTCGTTAC TTTCCACTAA ATAAAAGTTA AGTATGTGGT TCCCAGCCCA         783

GTGTTGTAAT GCTATGCCTA TGTAGTCAGT GTCTTGTTTG AGGGTGGAGA TGCTTAAAGG         843

GTGTGTCTTC ACAGTCCCAG CTTCGTAGTC TTTCAGCTTT ATGAATAAAT GATTTGCCTC         903

TTGCCTCTTT TATT                                                          917
```

( 2 ) INFORMATION FOR SEQ ID NO: 2:

( i ) SEQUENCE CHARACTERISTICS:
        ( A ) LENGTH: 221 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met Lys Thr Ala Thr Ala Val Val Leu Leu Leu Phe Ala Phe Thr Ser
 1               5                  10                  15

Lys Ser Tyr Phe Phe Gly Val Ala Asn Ala Ala Asn Ser Pro Val Leu
            20                  25                  30

Asp Thr Asp Gly Asp Glu Leu Gln Thr Gly Val Gln Tyr Tyr Val Leu
        35                  40                  45

Ser Ser Ile Ser Gly Ala Gly Gly Gly Leu Ala Leu Gly Arg Ala
    50                  55                  60

Thr Gly Gln Ser Cys Pro Glu Ile Val Val Gln Arg Arg Ser Asp Leu
65                  70                  75                  80

Asp Asn Gly Thr Pro Val Ile Phe Ser Asn Ala Asp Ser Lys Asp Asp
                85                  90                  95

Val Val Arg Val Ser Thr Asp Val Asn Ile Glu Phe Val Pro Ile Arg
                100                 105                 110

Asp Arg Leu Cys Ser Thr Ser Thr Val Trp Arg Leu Asp Asn Tyr Asp
            115                 120                 125

Asn Ser Ala Gly Lys Trp Trp Val Thr Thr Asp Gly Val Lys Gly Glu
        130                 135                 140

Pro Gly Pro Asn Thr Leu Cys Ser Trp Phe Lys Ile Glu Lys Ala Gly
145                 150                 155                 160

Val Leu Gly Tyr Lys Phe Arg Phe Cys Pro Ser Val Cys Asp Ser Cys
                165                 170                 175

Thr Thr Leu Cys Ser Asp Ile Gly Arg His Ser Asp Asp Gly Gln
                180                 185                 190

Ile Arg Leu Ala Leu Ser Asp Asn Glu Trp Ala Trp Met Phe Lys Lys
            195                 200                 205

Ala Ser Lys Thr Ile Lys Gln Val Val Asn Ala Asn Asp
        210                 215                 220
```

(2) INFORMATION FOR SEQ ID NO: 3:

(i) SEQUENCE CHARACTERISTICS:
    (A) LENGTH: 192 amino acids
    (B) TYPE: amino acid
    (D) TOPOLOGY: linear (ii) MOLECULE TYPE: protein (vi) ORIGINAL SOURCE:
    (A) ORGANISM: Theobroma cacao (ix) FEATURE:
    (A) NAME/KEY: Protein
    (B) LOCATION: 1..192
    (D) OTHER INFORMATION: /note= "21kD protein from T. cacao"

(xi) SEQUENCE DESCRIPTION: SEQ ID NO: 3:

```
Ala Asn Ser Pro Val Leu Asp Thr Asp Gly Asp Glu Leu Gln Thr Gly
 1               5                  10                  15

Val Gln Tyr Tyr Val Leu Ser Ser Ile Ser Gly Ala Gly Gly Gly Gly
                 20                  25                  30

Leu Ala Leu Gly Arg Ala Thr Gly Gln Ser Cys Pro Glu Ile Val Val
             35                  40                  45

Gln Arg Arg Ser Asp Leu Asp Asn Gly Thr Pro Val Ile Phe Ser Asn
         50                  55                  60

Ala Asp Ser Lys Asp Asp Val Val Arg Val Ser Thr Asp Val Asn Ile
 65                  70                  75                  80

Glu Phe Val Pro Ile Arg Asp Arg Leu Cys Ser Thr Ser Thr Val Trp
                 85                  90                  95

Arg Leu Asp Asn Tyr Asp Asn Ser Ala Gly Lys Trp Trp Val Thr Thr
             100                 105                 110

Asp Gly Val Lys Gly Glu Pro Gly Pro Asn Thr Leu Cys Ser Trp Phe
         115                 120                 125

Lys Ile Glu Lys Ala Gly Val Leu Gly Tyr Lys Phe Arg Phe Cys Pro
     130                 135                 140

Ser Val Cys Asp Ser Cys Thr Thr Leu Cys Ser Asp Ile Gly Arg His
145                 150                 155                 160

Ser Asp Asp Asp Gly Gln Ile Arg Leu Ala Leu Ser Asp Asn Glu Trp
             165                 170                 175

Ala Trp Met Phe Lys Lys Ala Ser Lys Thr Ile Lys Gln Val Val Asn
             180                 185                 190
```

(2) INFORMATION FOR SEQ ID NO: 4:

(i) SEQUENCE CHARACTERISTICS:
    (A) LENGTH: 181 amino acids
    (B) TYPE: amino acid
    (D) TOPOLOGY: linear (ii) MOLECULE TYPE: protein (vi) ORIGINAL SOURCE:
    (A) ORGANISM: BARLEY (ix) FEATURE:
    (A) NAME/KEY: Protein
    (B) LOCATION: 1..181
    (D) OTHER INFORMATION: /note= "ALPLHA-AMYLASE-SUBTILISIN INHIBITOR"

(xi) SEQUENCE DESCRIPTION: SEQ ID NO: 4:

```
Ala Asp Pro Pro Pro Val His Asp Thr Asp Gly His Glu Leu Arg Ala
 1               5                  10                  15
```

```
Asp  Ala  Asn  Tyr  Tyr  Val  Leu  Ser  Ala  Asn  Arg  Ala  His  Gly  Gly  Gly
               20                      25                      30

Leu  Thr  Met  Ala  Pro  Gly  His  Gly  Arg  His  Cys  Pro  Leu  Phe  Val  Ser
          35                      40                      45

Gln  Asp  Pro  Asn  Gly  Gln  His  Asp  Gly  Phe  Pro  Val  Arg  Ile  Thr  Pro
     50                      55                      60

Tyr  Gly  Val  Ala  Pro  Ser  Asp  Lys  Ile  Ile  Arg  Leu  Ser  Thr  Asp  Val
65                       70                      75                      80

Arg  Ile  Ser  Phe  Arg  Ala  Tyr  Thr  Thr  Cys  Leu  Gln  Ser  Thr  Glu  Trp
                    85                      90                      95

His  Ile  Asp  Ser  Glu  Leu  Ala  Ala  Gly  Arg  Arg  His  Val  Ile  Thr  Gly
                    100                     105                     110

Pro  Val  Lys  Asp  Pro  Ser  Pro  Ser  Gly  Arg  Glu  Asn  Ala  Phe  Arg  Ile
          115                     120                     125

Glu  Lys  Tyr  Ser  Gly  Ala  Glu  Val  His  Glu  Tyr  Lys  Leu  Met  Ser  Cys
     130                     135                     140

Gly  Asp  Trp  Cys  Gln  Asp  Leu  Gly  Val  Phe  Arg  Asp  Leu  Lys  Gly  Gly
145                      150                     155                     160

Ala  Trp  Phe  Leu  Gly  Ala  Thr  Glu  Pro  Tyr  His  Val  Val  Val  Phe  Lys
                    165                     170                     175

Lys  Ala  Pro  Pro  Ala
                    180
```

( 2 ) INFORMATION FOR SEQ ID NO: 5:

( i ) SEQUENCE CHARACTERISTICS:
( A ) LENGTH: 180 amino acids
( B ) TYPE: amino acid
( D ) TOPOLOGY: linear ( i i ) MOLECULE TYPE: protein ( v i ) ORIGINAL SOURCE:
( A ) ORGANISM: WHEAT ( i x ) FEATURE:
( A ) NAME/KEY: Protein
( B ) LOCATION: 1..180
( D ) OTHER INFORMATION: /note= "ALPHA-AMYLASE-SUBTILISIN INHIBITOR"

( x i ) SEQUENCE DESCRIPTION: SEQ ID NO: 5:

```
Asp  Pro  Pro  Pro  Val  His  Asp  Thr  Asp  Gly  Asn  Glu  Leu  Arg  Ala  Asp
1                   5                       10                      15

Ala  Asn  Tyr  Tyr  Val  Leu  Pro  Ala  Asn  Arg  Ala  His  Gly  Gly  Gly  Leu
               20                      25                      30

Thr  Met  Ala  Pro  Gly  His  Gly  Arg  Arg  Cys  Pro  Leu  Phe  Val  Ser  Gln
          35                      40                      45

Glu  Ala  Asp  Gly  Gln  Arg  Asp  Gly  Leu  Pro  Val  Arg  Ile  Ala  Pro  His
     50                      55                      60

Gly  Gly  Ala  Pro  Ser  Asp  Lys  Ile  Ile  Arg  Leu  Ser  Thr  Asp  Val  Arg
65                       70                      75                      80

Ile  Ser  Phe  Arg  Ala  Tyr  Thr  Thr  Cys  Val  Gln  Ser  Thr  Glu  Trp  His
                    85                      90                      95

Ile  Asp  Ser  Glu  Leu  Val  Ser  Gly  Arg  Arg  His  Val  Ile  Thr  Gly  Pro
                    100                     105                     110

Val  Arg  Asp  Pro  Ser  Pro  Ser  Gly  Arg  Glu  Asn  Ala  Phe  Arg  Ile  Glu
          115                     120                     125

Lys  Tyr  Ser  Gly  Ala  Glu  Val  His  Glu  Tyr  Lys  Leu  Ala  Ser  Cys  Gly
     130                     135                     140
```

```
Asp  Ser  Cys  Gln  Asp  Leu  Gly  Val  Phe  Arg  Asp  Leu  Lys  Gly  Gly  Ala
145                 150                      155                      160

Trp  Phe  Leu  Gly  Ala  Thr  Glu  Pro  Tyr  His  Val  Val  Val  Phe  Lys  Lys
                    165                      170                      175

Ala  Pro  Pro  Ala
               180
```

( 2 ) INFORMATION FOR SEQ ID NO: 6:

( i ) SEQUENCE CHARACTERISTICS:
        ( A ) LENGTH: 182 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: WINGED BEAN ( i x ) FEATURE:
        ( A ) NAME/KEY: Protein
        ( B ) LOCATION: 1..182
        ( D ) OTHER INFORMATION: /note= "CHYMOTRYPSIN INHIBITOR"

( x i ) SEQUENCE DESCRIPTION: SEQ ID NO: 6:

```
Asp  Asp  Asp  Leu  Val  Asp  Ala  Glu  Gly  Asn  Leu  Val  Glu  Asn  Gly  Gly
1                   5                   10                      15

Thr  Tyr  Tyr  Leu  Leu  Pro  His  Ile  Trp  Ala  His  Gly  Gly  Gly  Ile  Glu
               20                  25                      30

Thr  Ala  Lys  Thr  Gly  Asn  Glu  Pro  Cys  Pro  Leu  Thr  Val  Val  Arg  Ser
          35                       40                      45

Pro  Asn  Glu  Val  Ser  Lys  Gly  Glu  Pro  Ile  Arg  Ile  Ser  Ser  Gln  Phe
     50                       55                      60

Leu  Ser  Leu  Phe  Ile  Pro  Arg  Gly  Ser  Leu  Val  Ala  Leu  Gly  Phe  Ala
65                       70                      75                      80

Asn  Pro  Pro  Ser  Cys  Ala  Ala  Ser  Pro  Trp  Trp  Thr  Val  Val  Asp  Ser
               85                       90                      95

Pro  Gln  Gly  Pro  Ala  Val  Lys  Leu  Ser  Gln  Gln  Lys  Leu  Pro  Glu  Lys
               100                     105                     110

Asp  Ile  Leu  Val  Phe  Lys  Phe  Glu  Lys  Val  Ser  His  Ser  Asn  Ile  His
               115                     120                     125

Val  Tyr  Lys  Leu  Leu  Tyr  Cys  Gln  His  Asp  Glu  Glu  Asp  Val  Lys  Cys
          130                     135                     140

Asp  Gln  Tyr  Ile  Gly  Ile  His  Arg  Asp  Arg  Asn  Gly  Asn  Arg  Arg  Leu
145                      150                     155                     160

Val  Val  Thr  Glu  Glu  Asn  Pro  Leu  Glu  Leu  Val  Leu  Lys  Ala  Lys  Ser
                    165                     170                     175

Glu  Thr  Ala  Ser  Ser  His
                    180
```

( 2 ) INFORMATION FOR SEQ ID NO: 7:

( i ) SEQUENCE CHARACTERISTICS:
        ( A ) LENGTH: 171 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: WINGED BEAN ( i x ) FEATURE:

(A) NAME/KEY: Protein
            (B) LOCATION: 1..171
            (D) OTHER INFORMATION: /note= "TRYPSIN INHIBITOR"

(xi) SEQUENCE DESCRIPTION: SEQ ID NO: 7:

| Glu | Pro | Leu | Leu | Asp | Ser | Glu | Gly | Glu | Leu | Val | Arg | Asn | Gly | Gly | Thr |
|---|---|---|---|---|---|---|---|---|---|---|---|---|---|---|---|
| 1 | | | | 5 | | | | | 10 | | | | | 15 | |

| Tyr | Tyr | Leu | Leu | Pro | Asp | Arg | Trp | Ala | Leu | Gly | Gly | Gly | Ile | Glu | Ala |
|---|---|---|---|---|---|---|---|---|---|---|---|---|---|---|---|
| | | | 20 | | | | 25 | | | | | 30 | | | |

| Ala | Ala | Thr | Gly | Thr | Glu | Thr | Cys | Pro | Leu | Thr | Val | Val | Arg | Ser | Pro |
|---|---|---|---|---|---|---|---|---|---|---|---|---|---|---|---|
| | | 35 | | | | | 40 | | | | | 45 | | | |

| Asn | Glu | Val | Ser | Val | Gly | Glu | Pro | Leu | Arg | Ile | Ser | Ser | Gln | Leu | Arg |
|---|---|---|---|---|---|---|---|---|---|---|---|---|---|---|---|
| | 50 | | | | | 55 | | | | | 60 | | | | |

| Ser | Gly | Phe | Ile | Pro | Asp | Tyr | Ser | Leu | Val | Arg | Ile | Gly | Phe | Ala | Asn |
|---|---|---|---|---|---|---|---|---|---|---|---|---|---|---|---|
| 65 | | | | | 70 | | | | | 75 | | | | | 80 |

| Pro | Pro | Lys | Cys | Ala | Pro | Ser | Pro | Trp | Trp | Thr | Val | Val | Glu | Asp | Gln |
|---|---|---|---|---|---|---|---|---|---|---|---|---|---|---|---|
| | | | | 85 | | | | | 90 | | | | | 95 | |

| Pro | Gln | Gln | Pro | Ser | Val | Lys | Leu | Ser | Glu | Leu | Lys | Ser | Thr | Lys | Phe |
|---|---|---|---|---|---|---|---|---|---|---|---|---|---|---|---|
| | | | 100 | | | | | 105 | | | | | 110 | | |

| Asp | Tyr | Leu | Phe | Lys | Phe | Glu | Lys | Val | Thr | Ser | Lys | Phe | Ser | Ser | Tyr |
|---|---|---|---|---|---|---|---|---|---|---|---|---|---|---|---|
| | | 115 | | | | | 120 | | | | | 125 | | | |

| Lys | Leu | Lys | Tyr | Cys | Ala | Lys | Arg | Asp | Thr | Cys | Lys | Asp | Ile | Gly | Ile |
|---|---|---|---|---|---|---|---|---|---|---|---|---|---|---|---|
| | 130 | | | | | 135 | | | | | 140 | | | | |

| Tyr | Arg | Asp | Gln | Gly | Tyr | Ala | Arg | Leu | Val | Val | Thr | Asp | Glu | Asn | Pro |
|---|---|---|---|---|---|---|---|---|---|---|---|---|---|---|---|
| 145 | | | | | 150 | | | | | 155 | | | | | 160 |

| Leu | Val | Val | Ile | Phe | Lys | Lys | Val | Glu | Ser | Ser |
|---|---|---|---|---|---|---|---|---|---|---|
| | | | | 165 | | | | | 170 | |

(2) INFORMATION FOR SEQ ID NO: 8:

(i) SEQUENCE CHARACTERISTICS:
        (A) LENGTH: 181 amino acids
        (B) TYPE: amino acid
        (D) TOPOLOGY: linear (ii) MOLECULE TYPE: protein (vi) ORIGINAL SOURCE:
        (A) ORGANISM: SOYBEAN (ix) FEATURE:
        (A) NAME/KEY: Protein
        (B) LOCATION: 1..181
        (D) OTHER INFORMATION: /note= "TRYPSIN INHIBITOR"

(xi) SEQUENCE DESCRIPTION: SEQ ID NO: 8:

| Asp | Phe | Val | Leu | Asp | Asn | Glu | Gly | Asn | Pro | Leu | Glu | Asn | Gly | Gly | Thr |
|---|---|---|---|---|---|---|---|---|---|---|---|---|---|---|---|
| 1 | | | | 5 | | | | | 10 | | | | | 15 | |

| Tyr | Tyr | Ile | Leu | Ser | Asp | Ile | Thr | Ala | Phe | Gly | Gly | Ile | Arg | Ala | Ala |
|---|---|---|---|---|---|---|---|---|---|---|---|---|---|---|---|
| | | | 20 | | | | 25 | | | | | 30 | | | |

| Pro | Thr | Gly | Asn | Glu | Arg | Cys | Pro | Leu | Thr | Val | Val | Gln | Ser | Arg | Asn |
|---|---|---|---|---|---|---|---|---|---|---|---|---|---|---|---|
| | | 35 | | | | | 40 | | | | | 45 | | | |

| Glu | Leu | Asp | Lys | Gly | Ile | Gly | Thr | Ile | Ile | Ser | Ser | Pro | Tyr | Arg | Ile |
|---|---|---|---|---|---|---|---|---|---|---|---|---|---|---|---|
| | 50 | | | | | 55 | | | | | 60 | | | | |

| Arg | Phe | Ile | Ala | Glu | Gly | His | Pro | Leu | Ser | Leu | Lys | Phe | Asp | Ser | Phe |
|---|---|---|---|---|---|---|---|---|---|---|---|---|---|---|---|
| 65 | | | | | 70 | | | | | 75 | | | | | 80 |

| Ala | Val | Ile | Met | Leu | Cys | Val | Gly | Ile | Pro | Thr | Glu | Trp | Ser | Val | Val |
|---|---|---|---|---|---|---|---|---|---|---|---|---|---|---|---|
| | | | | 85 | | | | | 90 | | | | | 95 | |

| Glu | Asp | Leu | Pro | Glu | Gly | Pro | Ala | Val | Lys | Ile | Gly | Glu | Asn | Lys | Asp |
|---|---|---|---|---|---|---|---|---|---|---|---|---|---|---|---|
| | | | 100 | | | | | 105 | | | | | 110 | | |

|     |     |     |     |     |     |     |     |     |     |     |     |     |     |     |
| --- | --- | --- | --- | --- | --- | --- | --- | --- | --- | --- | --- | --- | --- | --- |
| Ala | Met | Asp | Gly | Trp | Phe | Arg | Leu | Glu | Arg | Val | Ser | Asp | Asp | Glu | Phe |
|     | 115 |     |     |     |     | 120 |     |     |     |     | 125 |     |     |     |
| Asn | Asn | Tyr | Lys | Leu | Val | Phe | Cys | Pro | Gln | Gln | Ala | Glu | Asp | Asp | Lys |
|     | 130 |     |     |     |     | 135 |     |     |     |     | 140 |     |     |     |
| Cys | Gly | Asp | Ile | Gly | Ile | Ser | Ile | Asp | His | Asp | Asp | Gly | Thr | Arg | Arg |
| 145 |     |     |     |     | 150 |     |     |     |     | 155 |     |     |     |     | 160 |
| Leu | Val | Val | Ser | Lys | Asn | Lys | Pro | Leu | Val | Val | Gln | Phe | Gln | Lys | Leu |
|     |     |     |     | 165 |     |     |     |     | 170 |     |     |     |     | 175 |     |
| Asp | Lys | Glu | Ser | Leu |
|     |     |     |     | 180 |

( 2 ) INFORMATION FOR SEQ ID NO: 9:

( i ) SEQUENCE CHARACTERISTICS:
        ( A ) LENGTH: 172 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Erythrina latissima ( i x ) FEATURE:
        ( A ) NAME/KEY: Protein
        ( B ) LOCATION: 1..172
        ( D ) OTHER INFORMATION: /note= "TRYPSIN INHIBITOR"

( x i ) SEQUENCE DESCRIPTION: SEQ ID NO: 9:

|     |     |     |     |     |     |     |     |     |     |     |     |     |     |     |     |
| --- | --- | --- | --- | --- | --- | --- | --- | --- | --- | --- | --- | --- | --- | --- | --- |
| Val | Leu | Leu | Asp | Gly | Asn | Gly | Glu | Val | Val | Gln | Asn | Gly | Gly | Thr | Tyr |
| 1   |     |     |     | 5   |     |     |     |     | 10  |     |     |     |     | 15  |     |
| Tyr | Leu | Leu | Pro | Gln | Val | Trp | Ala | Gln | Gly | Gly | Val | Gln | Leu | Ala |
|     |     |     | 20  |     |     |     |     | 25  |     |     |     |     | 30  |     |
| Lys | Thr | Gly | Glu | Glu | Thr | Cys | Pro | Leu | Thr | Val | Val | Gln | Ser | Pro | Asn |
|     |     | 35  |     |     |     |     | 40  |     |     |     |     | 45  |     |     |     |
| Glu | Leu | Ser | Asp | Gly | Lys | Pro | Ile | Arg | Ile | Glu | Ser | Arg | Leu | Arg | Ser |
|     | 50  |     |     |     |     | 55  |     |     |     |     | 60  |     |     |     |     |
| Thr | Phe | Ile | Pro | Asp | Asp | Asp | Glu | Val | Arg | Ile | Gly | Phe | Ala | Tyr | Ala |
| 65  |     |     |     |     | 70  |     |     |     |     | 75  |     |     |     |     | 80  |
| Pro | Lys | Cys | Ala | Pro | Ser | Pro | Trp | Trp | Thr | Val | Val | Glu | Asp | Glu | Gln |
|     |     |     |     | 85  |     |     |     |     | 90  |     |     |     |     | 95  |     |
| Glu | Gly | Leu | Ser | Val | Lys | Leu | Ser | Glu | Asp | Glu | Ser | Thr | Gln | Phe | Asp |
|     |     |     |     | 100 |     |     |     |     | 105 |     |     |     |     | 110 |     |
| Tyr | Pro | Phe | Lys | Phe | Glu | Gln | Val | Ser | Asp | Lys | Leu | His | Ser | Tyr | Lys |
|     |     | 115 |     |     |     |     | 120 |     |     |     |     | 125 |     |     |     |
| Leu | Leu | Tyr | Cys | Glu | Gly | Lys | His | Glu | Lys | Cys | Ala | Ser | Ile | Gly | Ile |
|     | 130 |     |     |     |     | 135 |     |     |     |     | 140 |     |     |     |     |
| Asn | Arg | Asp | Gln | Lys | Gly | Tyr | Arg | Arg | Leu | Val | Val | Thr | Glu | Asp | Asn |
| 145 |     |     |     |     | 150 |     |     |     |     | 155 |     |     |     |     | 160 |
| Pro | Leu | Thr | Val | Val | Leu | Lys | Lys | Asp | Glu | Ser | Ser |
|     |     |     |     | 165 |     |     |     |     | 170 |     |     |

( 2 ) INFORMATION FOR SEQ ID NO: 10:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:

( A ) ORGANISM: YEAST PYRUVATE KINASE GENE ( i x ) FEATURE:
 ( A ) NAME/KEY: CDS
 ( B ) LOCATION: 41..49

( x i ) SEQUENCE DESCRIPTION: SEQ ID NO: 10:

TTTACAAGAC ACCAATCAAA ACAAATAAAA CATCATCACA ATG TCT AGA  49
                   Met Ser Arg
                    1

( 2 ) INFORMATION FOR SEQ ID NO: 11:

( i ) SEQUENCE CHARACTERISTICS:
 ( A ) LENGTH: 3 amino acids
 ( B ) TYPE: amino acid
 ( D ) TOPOLOGY: linear ( i i ) MOLECULE TYPE: protein ( x i ) SEQUENCE DESCRIPTION: SEQ ID NO: 11:

Met Ser Arg
1

( 2 ) INFORMATION FOR SEQ ID NO: 12:

( i ) SEQUENCE CHARACTERISTICS:
 ( A ) LENGTH: 49 base pairs
 ( B ) TYPE: nucleic acid
 ( C ) STRANDEDNESS: single
 ( D ) TOPOLOGY: linear ( i i ) MOLECULE TYPE: cDNA ( v i ) ORIGINAL SOURCE:
 ( A ) ORGANISM: YEAST PYRUVATE KINASE GENE ( i x ) FEATURE:
 ( A ) NAME/KEY: CDS
 ( B ) LOCATION: 41..49

( i x ) FEATURE:
 ( A ) NAME/KEY: misc_feature
 ( B ) LOCATION: 6..11
 ( D ) OTHER INFORMATION: /function="Hin cloning site
   introduced"

( x i ) SEQUENCE DESCRIPTION: SEQ ID NO: 12:

TTTACAAGCT TCCAATCAAA ACAAATAAAA CATCATCACA ATG TCT AGA  49
                   Met Ser Arg
                    1

( 2 ) INFORMATION FOR SEQ ID NO: 13:

( i ) SEQUENCE CHARACTERISTICS:
 ( A ) LENGTH: 3 amino acids
 ( B ) TYPE: amino acid
 ( D ) TOPOLOGY: linear ( i i ) MOLECULE TYPE: protein ( x i ) SEQUENCE DESCRIPTION: SEQ ID NO: 13:

Met Ser Arg
1

( 2 ) INFORMATION FOR SEQ ID NO: 14:

( i ) SEQUENCE CHARACTERISTICS:
 ( A ) LENGTH: 33 base pairs
 ( B ) TYPE: nucleic acid
 ( C ) STRANDEDNESS: single
 ( D ) TOPOLOGY: linear ( i i ) MOLECULE TYPE: cDNA ( i x ) FEATURE:
                    ( A ) NAME/KEY: misc_feature
                    ( B ) LOCATION: 1..33
                    ( D ) OTHER INFORMATION: /product="Hin-Nco linker"

( x i ) SEQUENCE DESCRIPTION: SEQ ID NO: 14:

AGCTTCCAAT CAAAACAAAT AAAACATCAT CAC            33

( 2 ) INFORMATION FOR SEQ ID NO: 15:

( i ) SEQUENCE CHARACTERISTICS:
                    ( A ) LENGTH: 33 base pairs
                    ( B ) TYPE: nucleic acid
                    ( C ) STRANDEDNESS: single
                    ( D ) TOPOLOGY: linear ( i i ) MOLECULE TYPE: cDNA ( i x ) FEATURE:
                    ( A ) NAME/KEY: misc_feature
                    ( B ) LOCATION: 1..33
                    ( D ) OTHER INFORMATION: /product="Hin-Nco linker"

( x i ) SEQUENCE DESCRIPTION: SEQ ID NO: 15:

CATGGTGATG ATGTTTTATT TGTTTTGATT GGA            33

( 2 ) INFORMATION FOR SEQ ID NO: 16:

( i ) SEQUENCE CHARACTERISTICS:
                    ( A ) LENGTH: 49 base pairs
                    ( B ) TYPE: nucleic acid
                    ( C ) STRANDEDNESS: single
                    ( D ) TOPOLOGY: linear ( i i ) MOLECULE TYPE: cDNA ( i x ) FEATURE:
                    ( A ) NAME/KEY: CDS
                    ( B ) LOCATION: 41..49
                    ( D ) OTHER INFORMATION: /product="21kD EXPRESSION VECTOR A"

( x i ) SEQUENCE DESCRIPTION: SEQ ID NO: 16:

TTTACAAGCT TCCAATCAAA ACAAATAAAA CATCATCACC ATG GAG ACC            49
                                                                   Met Glu Thr
                                                                    1

( 2 ) INFORMATION FOR SEQ ID NO: 17:

( i ) SEQUENCE CHARACTERISTICS:
                    ( A ) LENGTH: 3 amino acids
                    ( B ) TYPE: amino acid
                    ( D ) TOPOLOGY: linear ( i i ) MOLECULE TYPE: protein ( x i ) SEQUENCE DESCRIPTION: SEQ ID NO: 17:

Met Glu Thr
 1

( 2 ) INFORMATION FOR SEQ ID NO: 18:

( i ) SEQUENCE CHARACTERISTICS:
                    ( A ) LENGTH: 27 base pairs
                    ( B ) TYPE: nucleic acid
                    ( C ) STRANDEDNESS: single
                    ( D ) TOPOLOGY: linear ( i i ) MOLECULE TYPE: DNA (genomic)

(vi) ORIGINAL SOURCE:
    (A) ORGANISM: YEAST ALPHA-FACTOR SIGNAL SEQUENCE (ix) FEATURE:
    (A) NAME/KEY: CDS
    (B) LOCATION: 1..27

(xi) SEQUENCE DESCRIPTION: SEQ ID NO: 18:

```
GAA  GGG  GTA  AGC  TTG  GAT  AAA  AGA  GAG                              27
Glu  Gly  Val  Ser  Leu  Asp  Lys  Arg  Glu
 1                  5
```

(2) INFORMATION FOR SEQ ID NO: 19:

(i) SEQUENCE CHARACTERISTICS:
    (A) LENGTH: 9 amino acids
    (B) TYPE: amino acid
    (D) TOPOLOGY: linear (ii) MOLECULE TYPE: protein (xi) SEQUENCE DESCRIPTION: SEQ ID NO: 19:

```
Glu  Gly  Val  Ser  Leu  Asp  Lys  Arg  Glu
 1                  5
```

(2) INFORMATION FOR SEQ ID NO: 20:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: misc_feature
    (B) LOCATION: 1..17
    (D) OTHER INFORMATION: /product="Hin-Nco linker"

(xi) SEQUENCE DESCRIPTION: SEQ ID NO: 20:

```
AGCTTGGATA AAAGAGC                                                       17
```

(2) INFORMATION FOR SEQ ID NO: 21:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: misc_feature
    (B) LOCATION: 1..17
    (D) OTHER INFORMATION: /product="Hin-Nco linker"

(xi) SEQUENCE DESCRIPTION: SEQ ID NO: 21:

```
CATGGCTCTT TTATCCA                                                       17
```

(2) INFORMATION FOR SEQ ID NO: 22:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: cDNA (ix) FEATURE:

( A ) NAME/KEY: CDS
                    ( B ) LOCATION: 1..36
                    ( D ) OTHER INFORMATION: /product="IN-PHASE FUSION OF 21kD
                          CODING REGION ( x i ) SEQUENCE DESCRIPTION: SEQ ID NO: 22:

```
GAA GGG GTA AGC TTG GAT AAA AGA GCC ATG GCA AAC                    36
Glu Gly Val Ser Leu Asp Lys Arg Ala Met Ala Asn
 1               5                   10
```

( 2 ) INFORMATION FOR SEQ ID NO: 23:

( i ) SEQUENCE CHARACTERISTICS:
                    ( A ) LENGTH: 12 amino acids
                    ( B ) TYPE: amino acid
                    ( D ) TOPOLOGY: linear ( i i ) MOLECULE TYPE: protein ( x i ) SEQUENCE DESCRIPTION: SEQ ID NO: 23:

```
Glu Gly Val Ser Leu Asp Lys Arg Ala Met Ala Asn
 1               5                   10
```

( 2 ) INFORMATION FOR SEQ ID NO: 24:

( i ) SEQUENCE CHARACTERISTICS:
                    ( A ) LENGTH: 11 amino acids
                    ( B ) TYPE: amino acid
                    ( D ) TOPOLOGY: linear ( i i ) MOLECULE TYPE: protein ( x i ) SEQUENCE DESCRIPTION: SEQ ID NO: 24:

```
Ala Asn Ser Pro Leu Asp Thr Asp Gly Asp Glu
 1               5                   10
```

( 2 ) INFORMATION FOR SEQ ID NO: 25:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( i i ) MOLECULE TYPE: cDNA ( i x ) FEATURE:
                    ( A ) NAME/KEY: misc_feature
                    ( B ) LOCATION: 1..17
                    ( D ) OTHER INFORMATION: /product="N at position 3 = C or T
                          N at position 6 = C, T, A or G
                          N at position 9 = C or T
                          N at position 12 = C, T, A or G
                          N at position 15 = C or T"

( x i ) SEQUENCE DESCRIPTION: SEQ ID NO: 25:

GANACNGANG GNGANGA                                                 17

( 2 ) INFORMATION FOR SEQ ID NO: 26:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( i i ) MOLECULE TYPE: cDNA ( i x ) FEATURE:
                    ( A ) NAME/KEY: misc_feature
                    ( B ) LOCATION: 1..17
                    ( D ) OTHER INFORMATION: /product="mutagenic primer"

( x i ) SEQUENCE DESCRIPTION: SEQ ID NO: 26:

ACTTAACCAT GGAGACC                                                                                                17

( 2 ) INFORMATION FOR SEQ ID NO: 27:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: misc_feature
  ( B ) LOCATION: 1..29
  ( D ) OTHER INFORMATION: /product="mutagenic primer"

( x i ) SEQUENCE DESCRIPTION: SEQ ID NO: 27:

TGGAGACTGC CATGGCAAAC TCTCCTGTG                                                                    29

( 2 ) INFORMATION FOR SEQ ID NO: 28:

( i ) SEQUENCE CHARACTERISTICS:
  ( A ) LENGTH: 14 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 28:

GGAGACTGCC ATGG                                                                                           14

RECOMBINANT 21 KD COCOA PROTEIN AND PRECURSOR

This invention relates to proteins and nucleic acids derived from or otherwise related to cocoa.

The beans of the cocoa plant (*Theobroma cacao*) are the raw material for cocoa, chocolate and natural cocoa and chocolate flavouring. As described by Rohan ("Processing of Raw Cocoa for the Market", FAO/UN (1963)), raw cocoa beans are extracted from the harvested cocoa pod, from which the placenta is normally removed, the beans are then "fermented" for a period of days, during which the beans are killed and a purple pigment is released from the cotyledons. During fermentation "unknown" compounds are formed which on roasting give rise to characteristic cocoa flavour. Robart suggests that polyphenols and theobromine are implicated in the flavour precursor formation. After fermentation, the beans are dried, during which time the characteristic brown pigment forms, and they are then stored and shipped.

Biehl et al, 1982 investigated proteolysis during anaerobic cocoa seed incubation and identified 26 kD and 44 kD proteins which accumulated during seed ripening and degraded during germination. Biehl asserted that there were storage proteins and suggested that they may give rise to flavour-specific peptides.

Biehl et al., 1985 again asserted that amino acids and peptides were important for flavours.

Fritz et al, 1985 identified polypeptides of 20 kD and 28 kD appearing in the cytoplasmic fraction of cocoa seed extracts at about 100 days after pollination. It appears that the 20 kD protein is thought to have glyceryl acyltransferase activity.

Pettipher et al., 1990 suggested that peptides are important for cocoa flavour and refers to 48 kD and 28 kD storage proteins.

In spite of the uncertainties in the art, as summarised above, proteins apparently responsible for flavour production in cocoa beans have now been identified. Further, it has been discovered that, in spite of Fritz's caution that "cocoa seed mRNA levels are notably low compared to other plants" (loc. cit.), it is possible to apply the techniques of recombinant DNA techniques to the production of such proteins.

According to a first aspect of the invention, there is provided a 23 kD protein of *Th. cacao* or a fragment thereof.

The 23 kD protein may be processed in vivo to form a 21 kD polypeptide.

According to a second aspect of the invention, there is provided a 21 kD protein of *Th. cacao* or a fragment thereof.

The term "fragment" as used herein and as applied to proteins or peptides indicates a sufficient number of amino acid residues are present for the fragment to be useful. Typically, at least four, five, six or even at least 10 or 20 amino acids may be present in a fragment. Useful fragments include those which are the same as or similar or equivalent to those naturally produced during the fermentation phase of cocoa bean processing. It is believed that such fragments take part in Maillard reactions during roasting, to form at least some of the essential flavour components of cocoa.

Proteins in accordance with the invention may be synthetic; they may be chemically synthesised or, preferably, produced by recombinant DNA techniques. Proteins produced by such techniques can therefore be termed "recombinant proteins". Recombinant proteins may be glycosylated or non-glycosylated; non-glycosylated proteins will result from prokaryotic expression systems. *Theobroma cacao* has two primary subspecies, *Th. cacao cacao* and *Th. cacao sphaerocarpum*. While proteins in accordance with the invention may be derived from these subspecies, the invention is not limited solely to these subspecies. For example, many cocoa varieties are hybrids between different species; an example of such a hybrid is the trinitario variety.

The invention also relates to nucleic acid, particularly DNA, coding for the proteins referred to above (whether the primary translation products, the processed proteins or fragments). The invention therefore also provides, in further aspects:

nucleic acid coding for a 23 kD protein of *Th. cacao* or for a fragment thereof; and nucleic acid coding for a 21 kD protein of *Th. cacao* or for a fragment thereof.

Included in the invention is nucleic acid which is degenerate for the wild type protein and which codes for conservative or other non-deleterious mutants. Nucleic acid which hybridises to the wild type material is also included.

Nucleic acid within the scope of the invention will generally be recombinant nucleic acid and may be in isolated form. Frequently, nucleic acid in accordance with the invention will be incorporated into a vector (whether an expression vector or otherwise) such as a plasmid. Suitable expression vectors will contain an appropriate promoter, depending on the intended expression host. For yeast, an appropriate promoter is the yeast pyruvate kinase (PK) promoter; for bacteria an appropriate promoter is a strong lambda promoter.

Expression may be secreted or non-secreted. Secreted expression is preferred, particularly in eukaryotic expression systems; an appropriate signal sequence may be present for this purpose. Signal sequences derived from the expression host (such as that from the yeast alpha-factor in the case of yeast) may be more appropriate than native cocoa signal sequences.

The invention further relates to host cells comprising nucleic acid as described above. Genetic manipulation may for preference take place in prokaryotes. Expression will for preference take place in a food-approved host. The yeast *Saccharomyces cerevisiae* is particularly preferred.

The invention aim relates to processes for preparing nucleic acid and protein as described above by nucleic acid replication and expression, respectively.

cDNA in accordance with the invention may be useful not only for obtaining protein expression but also for Restriction Fragment Length Polymorphism (RFLP) studies. In such studies, detectably labelled cDNA (eg radiolabelled) is prepared. DNA of a cultivar under analysis is then prepared and digested with restriction enzymes. Southern blotting with the labelled cDNA may then enable genetic correlations to be made between cultivars. Phenotypic correlations may then be deduced.

The invention will now be illustrated by the following non-limiting examples. The examples refer to the accompanying drawings, in which:

FIG. 1 shows a map of a full length cDNA clone hybridising with an oligonucleotide probe for the 21 kD protein, together with the regions covered by DNA sequencing;

FIGS. 2A and 2B (SEQ ID NOS: 1 and 2) show the DNA sequence of cDNA coding for the 21 kD protein and the presumed amino-acid sequence of the encoded 23 kD precursor;

FIGS. 3A and 3B (SEQ ID NOS: 3–9) show the relationship between the 21 kD protein and trypsin inhibitors from other plants;

FIG. 4 which includes (SEQ ID NO: 28) shows a map of plasmid pJLA502;

FIG. 5 shows two yeast expression vectors useful in the present invention; vector A is designed for internal expression and vector B is designed for secreted expression;

FIG. 6a (SEQ ID NOS: 10–17) shows, in relation to vector A, part of the yeast pyruvate kinase gene showing the vector A cloning site, and the use of Hin-Nco linkers to splice in the 21 kD gene;

FIG. 6b (SEQ ID NOS: 18–23) shows, in relation to vector B, part of the yeast alpha-factor signal sequence showing the vector B cloning site, and the use of Hin-Nco linkers to create an in-phase fusion; and FIG. 7 shows a map of plasmids pMY9 and pMY10, referred to in Example 16.

EXAMPLES

Example 1

Identification of the Major Seed Proteins

Figure 1:
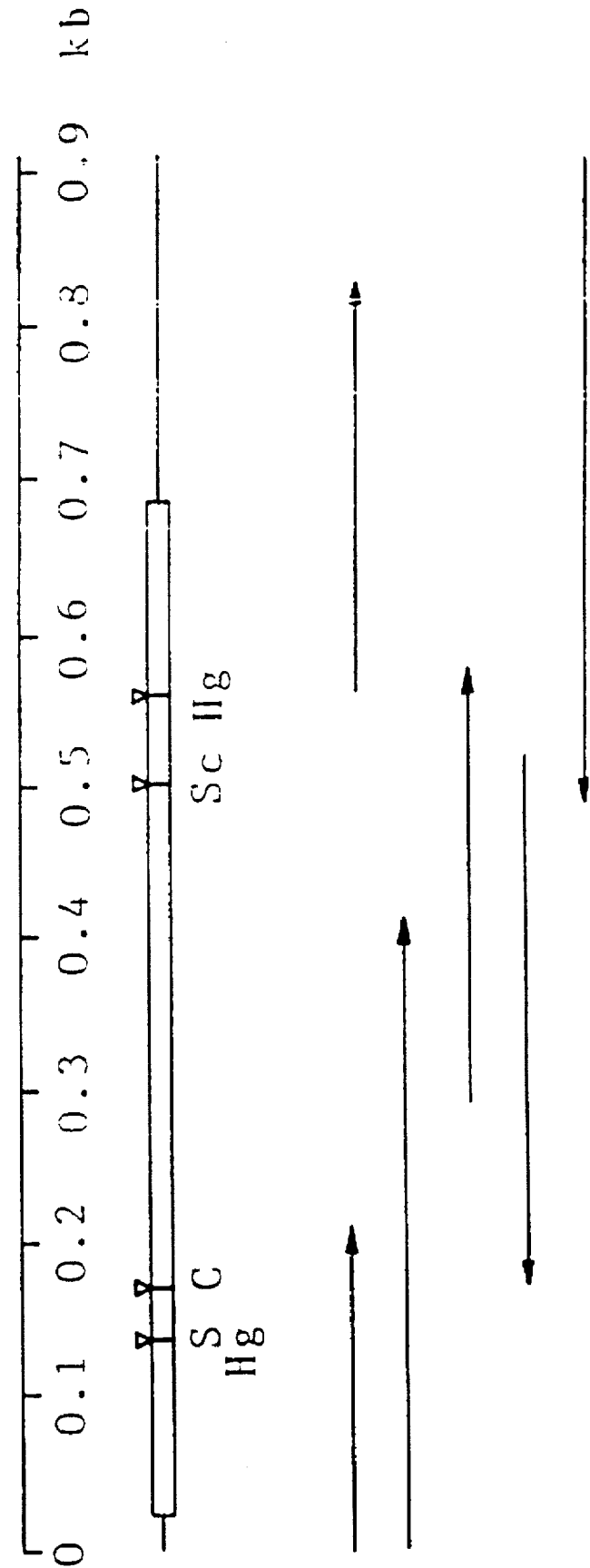

It is not practicable to extract proteins directly from cocoa beans due to the high fat and polyphenol contents, and proteins were, therefore, extracted from acetone powders made as follows. Mature beans from cocoa of West African origin (*Theobroma cacao amelonada*) were lyophilised and ground roughly in a pestle and mortar. Lipids were extracted by Soxhlet extraction with diethyl ether for two periods of four hours, the beans being dried and further ground between extractions. Polyphenols and pigments were then removed by several extractions with 80% acetone, 0.1% thioglycollic acid. After extraction the resulting paste was dried under vacuum and ground to a fine powder.

Total proteins were solubilised by grinding the powder with extraction buffer (0.05M sodium phosphate, pH 7.2; 0.01M 2-mercaptoethanol; 1% SDS) in a hand-held homogeniser, at 5 mg/ml. The suspension was heated at 95° C. for 5 minutes, and centrifuged at 18K for 20 minutes to remove insoluble material. The resulting clear supernatant contained about 1 mg/ml total protein. Electrophoresis of 25 μl on an SDS-PAGE gel (Laemmli, 1970) gave three major bands, including one at 21 kD, comprising approximately 30% of the total proteins. The 21 kD protein is presumed to be the polypeptide subunit of a major storage protein.

Characteristics of the Storage Polypeptide

The solubility characteristics of the 21 kD polypeptide was roughly defined by one or two quick experiments. Dialysis of the polypeptide solution against SDS-free extraction buffer rendered some polypeptides insoluble, as judged by their ability to pass through a 0.22 micron membrane, whereas the 21 kD polypeptide remained soluble. Only the 21 kD polypeptide was extracted from the acetone powder by water and dilute buffers, showing that this protein could be classed as an albumin.

Purification of the major polypeptide

The 21 kD polypeptide was purified by two rounds of gel filtration on a SUPEROSE-12 column of the PHARMACIA Fast Protein Liquid Chromatography system (FPLC), or by electroelution of bands after preparative electro-phoresis. (The words SUPEROSE and PHARMACIA are trade marks.) Concentrated protein extracts were made from 50 mg acetone powder per ml of extraction buffer, and 1–2 ml loaded onto 2 mm thick SDS-PAGE gels poured without a comb. After electrophoresis the gel was surface stained in aqueous Coomassie Blue, and the major bands cut out with a scalpel. Gel slices were electroeluted into dialysis bags in electrophoresis running buffer at 15 V for 24 hours, and the dialysate dialysed further against 0.1% SDS. Samples could be concentrated by lyophilisation.

Example 2

Amino-acid Sequence Data from Protein

Protein samples (about 10 μg) were subjected to conventional N-terminal amino-acid sequencing. A 12 amino-acid sequence was obtained for the 21 kD protein, and this information was used to construct an oligonucleotide probe (Woods et at, 1982; Woods, 1984).

Example 3

Raising Antibodies to the 21 kD Polypeptide

Polyclonal antibodies were prepared using the methodology of Catty and Raykundalia (1988). The serum was aliquoted into 1 ml fractions and stored at −20° C.

Characterising Antibodies to the 21 kD Polypeptide

Serum was immediately characterised using the Ochterloney double-diffusion technique, whereby antigen and antibody are allowed to diffuse towards one another from wells cut in agarose in borate-saline buffer. Precipitin lines are formed where the two interact if the antibody 'recognises' the antigen. This test showed that antibodies to the 21 kD protein antigen had been formed.

The gamma-globulin fraction of the serum was partially purified by precipitation with 50% ammonium sulphate, solubilisation in phosphate-buffered saline (PBS) and chromatography on a DE 52 cellulose ion-exchange column as described by Hill, 1984. Fractions containing gamma-globulin were monitored at 280 nm ($OD_{280}$ of 1.4 is equivalent to 1 mg/ml gamma-globulin) and stored at −20° C.

The effective titre of the antibodies was measured using an enzyme-linked immunosorbant assay (ELISA). The wells of a polystyrene microtitre plate were coated with antigen (10–1000 ng) overnight at 4° C. in carbonate coating buffer. Wells were washed in PBS-Tween and the test gamma globulin added at concentrations of 10, 1 and 0.1 μg/ml (approximately 1:100, 1:1000 and 1:10,000 dilutions). The diluent was PBS-Tween containing 2% polyvinyl pyrrolidone (PVP) and 0.2% BSA. Controls were preimmune serum from the same animal. Binding took place at 37° C. for 3–4 hours. The wells were washed as above and secondary antibody (goat anti-rabbit IgG conjugated to alkaline phosphatase) added at a concentration of 1 μg/ml, using the same conditions as the primary antibody. The wells are again washed, and alkaline phosphatase substrate (p-nitrophenyl phosphate; 0.6 mg/ml in diethanoi-amine buffer pH 9.8) added. The yellow colour, indicating a positive reaction, was allowed to develop for 30 minutes and the reaction stopped with 3M NaOH. The colour is quantified at 405 nm. More detail of this method is given in Hill, 1984. The method confirmed that the antibodies all had a high titre and could be used at 1 μg/ml concentration.

Example 4

Isolation of Total RIVA from Immature Cocoa Beans

The starting material for RNA which should contain a high proportion of mRNA specific for the storage proteins was immature cocoa beans, at about 130 days after pollination. Previous work had suggested that synthesis of storage proteins was approaching its height by this date (Biehl et al, 1982). The beans are roughly corrugated and pale pinkish-purple at this age.

The initial requirement of the total RNA preparation from cocoa beans was that it should be free from contaminants, as judged by the UV spectrum, particularly in the far UV, where a deep trough at 230 nm (260 nm:230 nm ratio is approximately 2.0) is highly diagnostic of clean RNA, and is intact, as judged by agarose gel electrophoresis of heat-denatured samples, which should show clear rRNA bands. A prerequisite for obtaining intact RNA is scrupulous cleanliness and rigorous precautions against RNases, which are ubiquitous and extremely stable enzymes. Glassware is customarily baked at high temperatures, and solutions and apparatus treated with the RNase inhibitor diethyl pyrocarbonate (DEPC, 0.1%) before autoclaving.

The most routine method for extraction of plant (and animal) RNA is extraction of the proteins with phenol/chloroform in the presence of SDS to disrupt protein-nucleic acid complexes, and inhibit the RNases which are abundant in plant material. Following phenol extraction the RNA is pelletted on a caesium chloride gradient before or after ethanol precipitation. This method produced more or less intact RNA, but it was heavily contaminated with dark brown pigment, probably oxidised polyphenols and tannins, which always co-purified with the RNA. High levels of polyphenols are a major problem in Theobroma tissues.

A method was therefore adopted which avoided the use of phenol, and instead used the method of Hall et al. (1978) which involves breaking the tissue in hot SDS-borate buffer, digesting the proteins with proteinase K, and specifically precipitating the RNA with LiCl. This method gave high yields of reasonably clean, intact RNA. Contaminants continued to be a problem and the method was modified by introducing repeated LiCl precipitation steps, the precipitate being dissolved in water and clarified by microcentrifugation after each step. This resulted in RNA preparations with ideal spectra, which performed well in subsequent functional tests such as in vitro translation.

Preparation of mRNA From Total RNA

The mRNA fraction was separated from total RNA by affinity chromatography on a small (1 ml) oligo-dT column, the mRNA binding to the column by its polyA tail. The RNA (1-2 mg) was denatured by heating at 65° C. and applied to the column in a high salt buffer. Poly A+ was eluted with low salt buffer, and collected by ethanol precipitation. The method is essentially that of Aviv and Leder (1972), modified by Maniatis et al (1982). From 1 mg of total RNA, approximately 10-20 µg polyA+ RNA was obtained (1-2%).

In vitro Translation of mRNA

The ability of mRNA to support in vitro translation is a good indication of its cleanliness and intactness. Only mRNAs with an intact polyA tail (3' end) will be selected by the oligo-dT column, and only mRNAs which also have an intact 5' end (translational start) will translate efficiently. In vitro translation was carried out using RNA-depleted wheat-germ lysate (Amersham International), the de novo protein synthesis being monitored by the incorporation of [$^{35}$S]-methionine (Roberts and Paterson, 1973). Initially the ram of de novo synthesis was measured by the incorporation of [$^{35}$S]-methionine into TCA-precipitable material trapped on glass fibre filters (GFC, Whatman). The actual products of translation were investigated by running on SDS-PAGE, soaking the gel in fluor, drying the gel and autoradiography. The mRNA preparations translated efficiently and the products covered a wide range of molecular weights, showing that intact mRNAs for even the largest proteins had been obtained. None of the major translation products corresponded in size to the 21 kD polypeptide identified in mature beans, and it was apparent that considerable processing of the nascent polypeptide must occur to give the mature form.

Example 5

Identification of Precursor to the Mature Polypeptide by Immunoprecipitation

Because the 21 kD storage polypeptides was not apparent amongst the translation products of mRNA from developing cocoa beans, the technique of immunoprecipitation, with specific antibodies raised to the 21 kD polypeptide, was used to identify the precursors from the translation mixture. This was done for two reasons: first to confirm that the appropriate mRNA was present before cloning, and second to gain information on the expected size of the encoding gene.

Immunoprecipitation was by the method of Cuming et al, 1986. [$^{35}$S]-labelled in vitro translation products were dissociated in SDS, and allowed to bind with specific antibody in PBS plus 1% BSA. The antibody-antigen mixture was then mixed with protein A-SEPHAROSE and incubated on ice to allow the IgG to bind to protein A. The slurry was poured into a disposable 1 ml syringe, and unbound proteins removed by washing with PBS+1% NONIDET P-40. The bound antibody was eluted with 1M acetic acid and the proteins precipitated with TCA. The antibody-antigen complex was dissociated in SDS, and subject to SDS-PAGE and fluorography, which reveals which labelled antigens have bound to the specific antibodies.

The results showed that the anti-21 kD antibody precipitated a 23 kD precursor. The precursor size corresponded to a major band on the in vitro translation products.

Example 6 cDNA Synthesis From the mRNA Preparations cDNA synthesis was carried out using a kit from Amersham International. The first strand of the cDNA is synthesised by the enzyme reverse transcriptase, using the four nucleotide bases found in DNA (dATP, dTTP, dGTP, dCTP) and an oligo-dT primer. The second strand synthesis was by the method of Gubler and Hoffman (1983), whereby the RNA strand is nicked in many positions by RNase H, and the remaining fragments used to prime the replacement synthesis of a new DNA strand directed by the enzyme E. coli DNA polymerase I. Any 3' overhanging ends of DNA are filled in using the enzyme T4 polymerase. The whole process was monitored by adding a small proportion of [$^{32}$P]-dCTP into the initial nucleotide mixture, and measuring the percentage incorporation of label into DNA. Assuming that cold nucleotides are incorporated at the same rate, and that the four bases are incorporated equally, an estimate of the synthesis of cDNA can be obtained. From 1 µg of mRNA approximately 140 ng of cDNA was synthesised. The products were analysed on an alkaline 1.4% agarose gel as described in the Amersham methods. Globin cDNA, synthesised as a control with the kit, was run on the same gel, which was dried down and autoradiographed. The cocoa cDNA had a range of molecular weights, with a substantial amount larger than the 600 bp of the globin cDNA.

Example 7

Cloning of cDNA into a Plasmid Vector by Homopolymer Tailing

The method of cloning cDNA into a plasmid vector was to 3' tail the cDNA with dC residues using the enzyme terminal transferase (Boehringer Corporation Ltd), and anneal into a PstI-cut and 5' tailed plasmid (Maniatis et al, 1982 Eschenfeldt et al, 1987). The optimum length for the dC tail is 12-20 residues. The tailing reaction (conditions as described by the manufacturers) was tested with a 1.5 kb blunt-ended restriction fragment, taking samples at intervals, and monitoring the incorporation of a small amount of [$^{32}$P]-dCTP. A sample of cDNA (70 ng) was then tailed using the predetermined conditions.

A dG-tailed plasmid vector (3+-oligo(dG)-tailed pUC9) was purchased from Pharmacia. 15 ng vector was annealed with 0.5–5 ng of cDNA at 58° C. for 2 hours in annealing buffer: 5 mM, Tris-HCl pH 7.6; 1 mM EDTA, 75 mM NaCl in a total volume of 50 µl. The annealed mixture was transformed into *E. coli* RRI (Bethesda Research Laboratories), transformants being selected on L-agar+100 µg/ml ampicillin. Approximately 200 transformants per ng of cDNA were obtained. Transformants were stored by growing in 100 µl L-broth in the wells of microtitre plates, adding 100 µl 80% glycerol, and storing at −20° C.

Some of the dC tailed cDNA was size selected by electrophoresing on a 0.8% agarose gel, cutting slits in the gel at positions corresponding to 0.5, 1.0 and 1.5 kb, inserting DE81 paper and continuing electrophoresis until the cDNA had run onto the DE81 paper. The DNA was then eluted from the paper with high salt buffer, according to the method of Dretzen et al (1981).

Example 8

Construction of Oligonucleotide Probes for the 21 kD Gene

The N-terminus of the 21 kD polypeptide (SEQ ID NO: 24), as determined in Example 2 above, was Ala-Asn-Ser-Pro-Leu-Asp-Thr-Asp-Gly-Asp-Glu.

From this the optimum region for synthesising a probe of 17 residues was as follows:

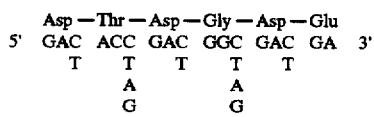

The 17-mer probe constructed is shown below the sequence (SEQ ID NO: 25): it is actually a mixture of 128 different 17-mers, one of which must be the actual coding sequence. Probe synthesis was carried out using an Applied Biosystems apparatus.

The 21 kD probe was purified by electrophoresis on a 20% acrylamide gel, the bands being detected by UV shadowing, and eluted by dialysing against water.

Example 9

Use of Oligonucleotides to Probe cDNA Library

The oligonucleotide probes were 5' end-labelled with gamma-[$^{32}$P]dATP and the enzyme polynucleotide kinase (Amersham International). The method was essentially that of Woods (1982, 1984), except that a smaller amount of isotope (15 µCi) was used to label about 40 ng probe, in 10 mM MgCl$_1$, 100 mM Tris-HCl, pH 7.6; 20 mM 2-mercaptoethanol.

The cDNA library was grown on GeneScreen (New England Nuclear) nylon membranes placed on the surface of L-agar+100 µg/ml ampicillin plates. (The word GeneScreen is a trade mark.) Colonies were transferred from microtitre plates to the membranes using a 6×8 multi-pronged device, designed to fit into the wells of half the microtitre plate. Colonies were grown overnight at 37° C., lysed in sodium hydroxide and bound to membranes as described by Woods (1982, 1984). After drying the membranes were washed extensively in 3×SSC/0.1% SDS at 65° C., and hybridised to the labelled probe, using a HYBAID apparatus from Hybald Ltd, PO Box 82, Twickenham, Middlesex. (The word HYBAID is a trade mark.) Conditions for hybridisation were as described by Mason & Williams (1985), a $T_d$ being calculated for each oligonucleotide according to the formula:

$T_d$=4° C. per GC base pair+2° C. per AT base pair.

At mixed positions the lowest value is taken.

Hybridisation was carried out at $T_d$ −5° C. Washing was in 6×SSC, 0.1% SDS initially at room temperature in the HYBAID apparatus, then at the hybridisation temperature ($T_d$ −5° C.) for some hours, and finally at $T_d$ for exactly 2 minutes. Membranes were autoradiographed onto FUJI X-ray film, with intensifying screens at −70° C. (The word FUJI is a trade mark.) After 24 –48 hours positive colonies stood out as intense spots against a low background.

Example 10

Analysis of Positive Clones for the 21 kD Polypeptide

Several positive clones were obtained with the 21 kD probe, and most of these contained an insert of 0.9 kb when digested with PstI (the original vector PstI site is re-created by the dG/dC tailing procedure). The inserts had the same restriction pattern, and are easily large enough to encode the 23 kD precursor, and it therefore seemed likely that they represented full-length clones. A map of the inset is shown in FIG. 1.

The 0.9 kb PstI fragment was purified away from the vector by agarose gel electrophoresis onto DE81 paper (Dretzen et al, 1981), and about 500 ng was nick-translated using the Amersham nick-translation kit. The resulting probe was −4×10$^7$ cpm and 10$^6$ cpm were used for the subsequent probing of the cDNA library, using the hybridisation method described by Wahl and Berger (1987). The conditions of 50% formamide and 42° C. were used. Several more incomplete positive clones were obtained, which were used in subsequent sequencing.

Example 11

Sequencing the Cloned Inserts

The sequencing strategy was to clone the inserts, and where appropriate subclones thereof, into the multiple cloning site of the plasmids pTZ18R/pTZ19R (Pharmacia). These plasmids are based on the better-known vectors pUC18/19 (Norrander et al, 1983), but contain a single-stranded origin of replication from the filamentous phage fl. When superinfected with phages in the same group, the plasmid is induced to undergo single-stranded replication, and the single-strands are packaged as phages extruded into the medium. DNA can be prepared from these 'phages' using established methods for M13 phages (Miller, 1987), and used for sequencing by the method of Sanger (1977) using the reverse sequencing primer. The superinfecting phage used is a derivative of M13 termed M13K07, which replicates poorly and so does not compete well with the plasmid, and contains a selectable kanamycin-resistance marker. Detailed methods for preparing single-strands from the pTZ plasmids and helper phages are supplied by Pharmacia. DNA sequence was compiled and analysed using the Staden package of programs (Staden, 1986), on a PRIME 9955 computer. (The word PRIME is a trade mark.)

Example 12

Features of the 21 kD cDNA, and Deduced Amino-acid Sequence of the 23 kD Precursor

The DNA sequence of the 21 kD cDNA, and the presumed amino-acid sequence of the encoded 23 kD precursor is shown in FIG. 2. The cDNA is 917 bases, excluding the 3' poly A tail. The ATG start codon is at position 21, followed by an open reading frame of 221 codons, ending with a stop codon at position 684. This is followed by a 233-base untranslated region, which is relatively AT-rich (60%) and has several stop codons in all three frames. There are two polyadenylation signals (AATAAA) at positions 753 and 887 (Proudfoot and Brownlee, 1976). At position 99 the sequence corresponding to the oligonucleotide probe is found, and at 167 the Cla site found experimentally.

The presumed 23 kD precursor polypeptide comprises 221 amino-acids and a molecular weight of 24003. The mature N-terminus is found at position 27, and the first 26 residues are highly hydrophobic, characteristic of a signal sequence recognised by the proteins responsible for translocating newly-synthesised proteins across membranes in the process of compartmentalisation (Kreil, 1981). The mature protein has 195 residues and a molecular weight of 21223, in good agreement with that deduced from polyacrylamide gels. The amino-acid composition of the mature protein is typical of a soluble protein with 24% charged residues and about 20% hydrophobic residues.

Homologies Between the 21 kD Protein and Other Known Proteins

Figure 3A:
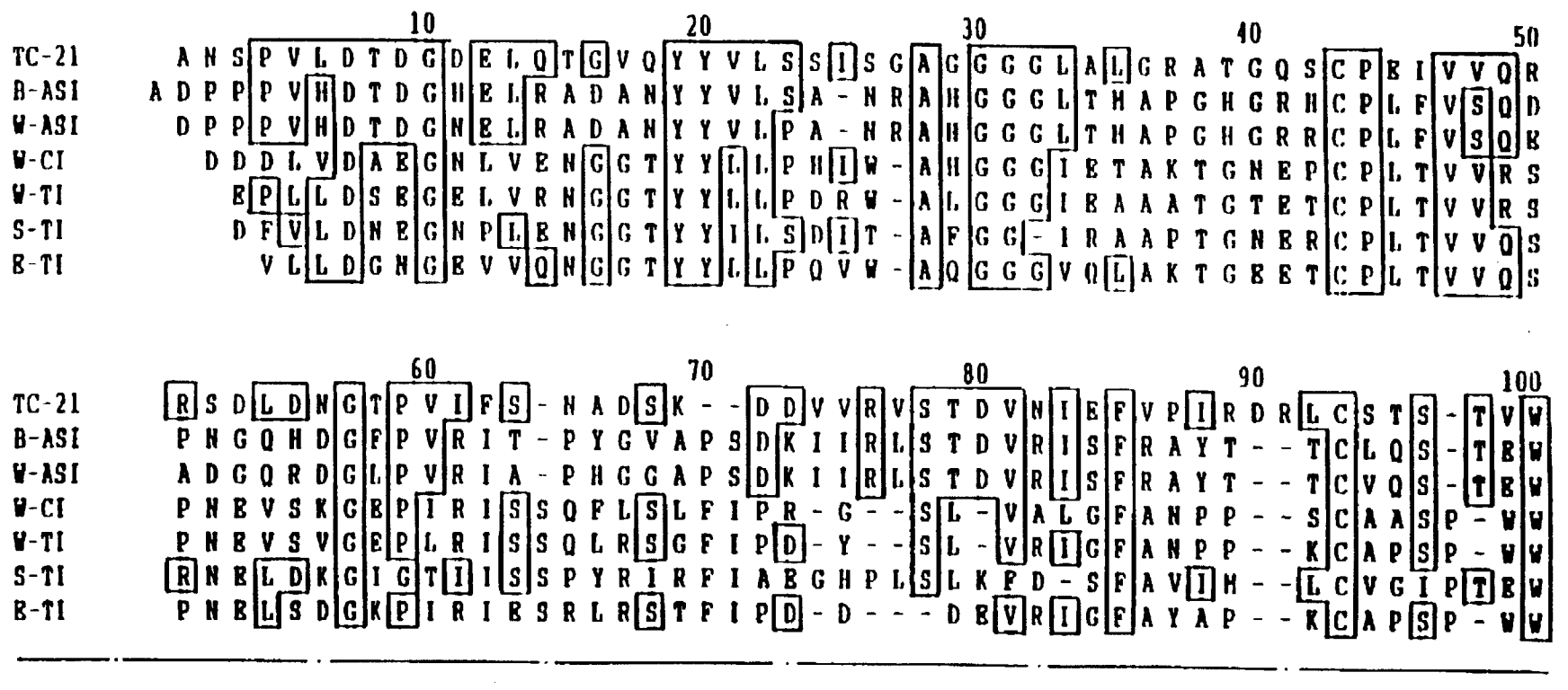
Figure 3B:
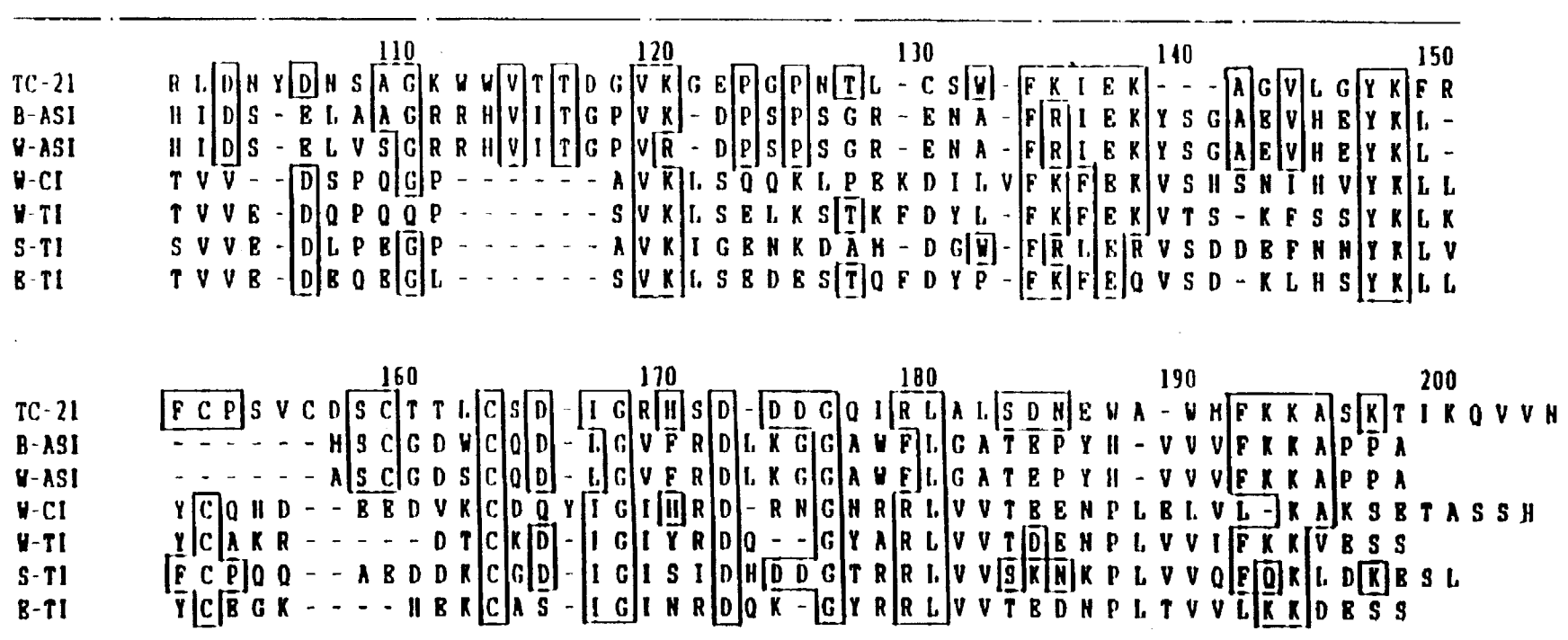

Searching the protein identification resource (PIR) databank (National Biomedical Research Foundation, Washington D.C.) using the sequence matching program FASTP (Lipman and Pearson, 1985), showed a high degree of homology between the 21 kD protein and Kunitz-type protease and α-amylase inhibitors found in large amounts in the seeds of several species, particularly legumes and cereals. Examples, shown in FIG. 3, include the barley α-amylase/subtilisin inhibitor, B-ASI (Svendsen et al. 1986), wheat α-amylase/subtilisin inhibitor, W-ASI (Maeda, 1986), winged bean (*Pscophocarpus tetragonolobus*) chymotrypsin inhibitor, W-CI (Shibata et al. 1988), winged bean trypsin inhibitor, W-TI (Yamamoto et al. 1983), soybean trypsin inhibitor, S-TI (Koide and Ikenaka, 1973b), *Erythrina latissima* trypsin inhibitor, E-TI (Joubert et al. 1985).

All the Kunitz-type inhibitors are of a similar size and align along their entire length. Thus the 21 kD protein must belong to this general class.

Example 13

**Expression of the 23 kD and 21 kD Polypeptides in *E. coli***

Figure 4:
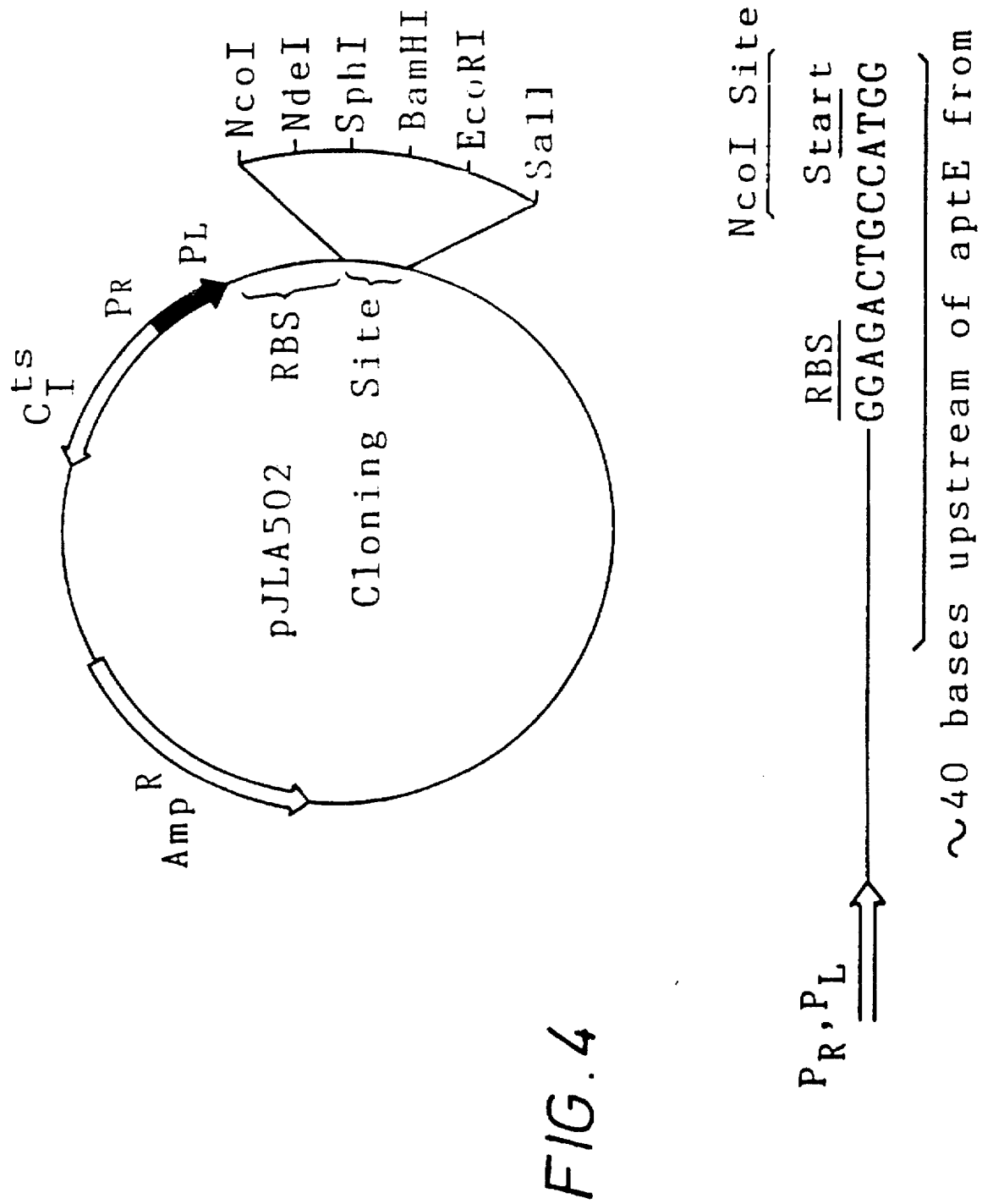

The DNA encoding the 23 kD and 21 kD polypeptides (ie. with and without the hydrophobic signal peptide) was subcloned into the *E. coli* expression vector, pJLA502 (Schauder et al, 1987) marketed by Medac GmbH, Postfach 303629, D-7000, Hamburg 36 (see FIG. 4). The vector contains the strong lambda promoters, $P_L$ and $P_R$, and the leader sequence and ribosome binding site of the very efficiently translated *E. coli* gene, atpE. It also contains a temperature-sensitive cI repressor, and so expression is repressed at 30° C. and activated at 42° C. The vector has an NcoI site (containing an ATG codon: CCATGG) correctly placed with respect to the ribosome binding site, and foreign coding sequences must be spliced in at this point. The 23 kD coding sequence does not have an NcoI site at the initial ATG, so one was introduced by in vitro mutagenesis.

In vitro mutagenesis was carried out using a kit marketed by Amersham International, which used the method of Eckstein and co-workers (Taylor et al, 1985). After annealing the mutagenic primer (SEQ ID NO: 26) to single-stranded DNA the second strand synthesis incorporates alpha-thio-dCTP in place of dCTP. After extension and ligation to form closed circles, the plasmid is digested with NciI, an enzyme which cannot nick DNA containing thio-dC. Thus only the original strand is nicked, and subsequently digested with exonuclease III. The original strand is then resynthesised, primed by the remaining DNA fragments and complementing the mutated position in the original strand. Plasmids are then transformed into *E. coli* and checked by plasmid mini preparations.

An NcoI site was introduced into the 23 kD cDNA in plasmid pMS101 (in the vector pTZ19R, so that single-stranded DNA could readily be produced) using the mutagenic primer: 5' ACTTAACCATGGAGACC 3', to create the plasmid pMS106. The primer was chosen to avoid extensive hybridisation elsewhere in the plasmid.

The 23 kD coding region was cloned into the *E. coli* expression vector pJLA502 on an NcoI-EcoI fragment (pMS107). The coding region was then cloned back into pTZ19 on a XhoI (upstream of the NcoI) -EcoRI fragment. This creates a pTZ-23 kD plasmid (pMS108) which has eliminated the poly G/C region, likely to disrupt transcription between the T7 promoter in the vector and the coding region. In vitro transcription, using T7 RNA polymerase, produced abundant RNA which translated in a wheat germ system to give a 23 kD protein. This proves that a functional gene, capable of producing a protein of the anticipated size, is present on the plasmid.

The hydrophobic sequel sequence was deleted from plasmid pMS108 using a mutagenic primer (SEQ ID NO: 27) designed to bind either side of the proposed deletion:

5' TGGAGACTGCCATGGCAAACTCTCCTGTG 3'

The resulting plasmid, pMS111, had retained an NcoI site at the ATG start, and the 21 kD coding region was subcloned into pJLA502 on an NcoI-BamHI fragment (pMS113).

The two expression vectors were transformed into *E. coli* UT580. The transformed strains were grown in L-broth+ampicillin (100 μg/ml) at 30° C. until log phase ($OD_{610}$=0.5) and the temperature was then shifted to 42° C. and samples taken at intervals. Samples were dissociated by boiling in SDS loading buffer, and run on SDS-PAGE gels. The proteins were electroblotted onto nitrocellulose membranes (Towbin et al, 1979) and Western blotting carried out using the anti-21 kD antibody prepared in Example 3 above (at 2 μg/ml) and as a secondary antibody, goat anti-rabbit -IgG conjugated to alkaline phosphatase (Scott et al, 1988).

For the vector pMS107 the antibody detected specific protein of molecular weight about 23 kD, but there were also smaller bands, including one at 21 kD suggesting that *E. coli* was partially cleaving the hydrophobic signal. The largest mount of protein was seen after 18 hours, and was the equivalent of at least 1-2 mg/l. Controls containing only the vector gave no immuno-detectable proteins. For the vector pMS113 a similar result was obtained, except that only the 21 kD protein was seen: there was no evidence of higher expression in the absence of the signal sequence. However transforming the vectors into the protease-deficient strain CAG629 (Dr C. A. Gross) resulted in a much higher level of expression in both cases, in the order of 5-10 mg/l.

Example 14

**Expression of the 21/23 kD Polypeptides in Yeast (*Saccharomyces cerevisiae*)**

Two yeast expression vectors were used, both based on a yeast-*E. coli* shuffle vector containing yeast and *E. coli* origins of replication, and suitable selectable markers (ampicillin-resistance for *E. coli* and leucine auxotrophy for yeast). Both vectors contain the yeast pyruvate kinase (PK) promoter and leader sequence and have a HindIII cloning site downstream of the promoter. One vector, A, is designed for internal expression, and the other, B, for secreted expression, having a portion of the signal sequence of the yeast mating alpha-factor downstream of the promoter, with a HindIII site within it to create fusion proteins with incoming coding sequences. The vectors are illustrated in FIG. 5.

To use the vectors effectively it is desirable to introduce the foreign coding region such that for vector A, the region from the HindIII cloning site to the ATG start is the same as the yeast PK gene, and for vector B, the remainder of the alpha-factor signal, including the lysine at the cleavage point. In practice this situation was achieved by synthesising two sets of HindIII-NcoI linkers to breach the gap between the HindIII cloning site in the vector and the NcoI at the ATG start of the coding sequence. For vector B, when the coding sequence is to be spliced to the yeast alpha-factor signal, the coding region of the 21 kD polypeptide (ie. with the cocoa signal sequence removed) was used. The constructs are illustrated in FIG. 6. For ease of construction of the yeast vectors, HindIII-NcoI linkers were first cloned into the appropriate pTZ plasmids, and HindIII-BamHI fragments containing linkers plus coding region cloned into the yeast vector.

The yeast expression plasmids were transferred into yeast spheroplasts using the method of Johnston (1988). The transformation host was the LEU⁻ strain AH22, and transformants were selected on leucine-minus minimal medium. LEU⁺ transformants were streaked to single colonies, which were grown in 50 ml YEPD medium (Johnston, 1988) at 28° C. for testing the extent and distribution of foreign protein. Cells were harvested from cultures in preweighed tubes in a bench-top centrifuge, and washed in 10 ml lysis buffer (200 mM Tris, pH 8.1; 10% glycerol). The cell medium was reserved and concentrated 10–25× in an AMICON mini concentrator. (The word AMICON is a trade mark.) The washed cells were weighed and resuspended in lysis buffer plus protease inhibitors (1 mM phenyl methyl sulphonyl fluoride (PMSF); 1 µg/ml aprotinin; 0.5 µg/ml leupeptin) at a concentration of 1 g/ml. 1 volume acid-washed glass-beads was added and the cells broken by vortexing for 8 minutes in total, in 1 minute bursts, with 1 minute intervals on ice. After checking under the microscope for cell breakage, the mixture was centrifuged at 7000 rpm for 3 minutes to pellet the glass buds. The supernatant was removed to a pre-chilled centrifuge tube, and centrifuged for 1 hour at 20,000 rpm. (Small samples can be centrifuged in a microcentrifuge in the cold.) The supernatant constitutes the soluble fraction. The pellet was resuspended in 1 ml lysis buffer plus 10% SDS and 1% mercaptoethanol and heated at 90° C. for 10 minutes. After centrifuging for 15 minutes in a microcentrifuge the supernatant constitutes the particulate fraction.

Samples of each fraction and the concentrated medium were examined by Western blotting. Plasmid pMS116, designed for internal expression, produced both 23 kD and 21 kD polypeptides in the soluble fraction of the cell lysate, and in the medium considerable amounts (2–5 mg/l) of the 21 kD polypeptide. Thus the yeast is recognising the cocoa signal sequence and transporting the protein across the membrane, cleaving the signal during the process. The cleavage site appears to be correct, judging by the size of the final protein.

Plasmid pMS117, designed for secreted expression, gave a rather similar result with rather more 21 kD polypeptide in the medium. No evidence of the uncleaved polypeptide with the yeast alpha-factor signal still attached was found, either in the soluble or particulate fraction.

Example 15

Scale-up of Production of the 21 kD Protein in a 5 L Fermenter

To assess the productivity of the 21 kD protein from yeast AH22 containing the plasmid pMS117 under scale-up conditions the strain was grown in a 5 L bioreactor manufactured by Life Technologies Inc. Like the small-scale growth experiments the medium used was YEPD, and the inoculum was 10 ml of a late log phase culture ($OD_{600}$ 4.0). The aeration rate was 2 L/min and the stirring speed 350 rpm, and to control the foaming caused by these aeration and stirring speeds 10 ml safflower oil was added. The cells were just entering log phase after 10 hours and by 15 hours the log phase was over with the disappearance of the glucose and accumulation of ethanol. However growth continued until the harvesting point at 60 hours, with the concomitant oxidation of the ethanol. The final biomass was 28 g/L wet weight, 7.3 g/L dry weight. Western blotting of the medium showed that 21 kD protein was exported to the medium slowly at first, but accumulated rapidly in late stationary phase rising to approximately 20–30 mg/L at the time of harvesting.

At the end of the experiment yeast cells were removed from the medium by cross-flow filtration through a 0.2 µm membrane, and the protein (or macromolecular) constituents in the medium were concentrated by cross-flow filtration through an ultra filtration membrane with a molecular weight cut-off of 10 kD. The crossflow filtration apparatus was manufactured by Sartorius GmbH, Goettingen, Germany. The 21 kD protein can be further crudely purified by precipitation with 80% ammonium sulphate, followed by redissolving in water and dialysis.

Some enhancement of the yield was obtained by a batch feed process whereby the glucose levels were topped up to 2% from a concentrated solution as soon as the glucose levels had dropped below 0.1%. Four such additions were made at 16, 23, 34 and 37 hours, and growth continued until 58 hours. Improved yields of the 21 kD protein were obtained, up to 50 mg/L by the end of the experiment.

Example 16

Expression of the 23 kD/21 kD Protein in *Hansenula polymorpha*

The methylotrophic yeast *Hansenula polymorpha* offers a number of advantages over *Saccharamyces cerevisiae* as a host for the expression of heterologous proteins (EP-A-0173378 and Sudbery et al, 1988). The yeast will grow on methanol as sole carbon source, and under these conditions the enzyme methanol oxidase (MOX) can represent up to 40% of the total cell protein. Thus the MOX promoter is a very powerful one that can be used in a vector to drive the synthesis of heterologous proteins, and it is effective even as a single copy. This gives the potential to use stable integrated vectors. Hansenula can also grow on rich carbon sources such as glucose, in which case the MOX promoter is completely repressed. This means that cells containing the heterologous gene can be grown to a high density on glucose, and induced to produce the foreign protein by allowing the glucose to run out and adding methanol.

Constructs (pMY10 and pMY9) containing a 21 kD or 23 kD gene sandwiched between a MOX promoter and MOX terminator were made in the yeast episomal plasmid YEp13. Both contained a yeast secretion signal from invertase spliced to the cocoa gene coding region, as illustrated in FIG. 7. These constructs were transformed into Hansenula and both secreted the 21/23 kD protein into the medium under inducing conditions, although pMY10, containing the yeast signal but not the plant signal, was the most effective.

The Hansenula construct pMY10 has also been grown under scale-up conditions in a fermenter, and biomass yields of 45 g/L dry weight were obtained after induction with methanol. After induction the 21 kD protein was found in the medium in increasing mounts up to 50 mg/L.

E. coli Strains

| | |
|---|---|
| RR1 | F⁻$v_B^-M_B^-$ ara-14 proA2 leuB6 lacY1 galK2 vpsL20 (str$^r$) xyl-5 mtl-1 supE44 |
| CAG629 | lac$_{am}$ typ$_{am}$ pho$_{am}$ htp$^R_{am}$ mal rpsL lon supC$_{ts}$ |
| UT580 | (lac-pro) supE thi hsdD5 I F'tra D36 proA $^+B^+$ lacI$^q$ lacZ M15 |

References

Aviv, H., and Leder, P. Proc. Natl. Acad. Sci. USA 69, 1408–1412 (1972). Purification of biologically active globin mRNA by chromatography on oligo dT cellulose Biehl, B., Wewetzer, C., and Passern, D. J. Sci. Food Agric. 33, 1291–1304 (1982). Vacuolar (Storage) Proteins of Cocoa Seeds and their Degradation during Germination and Fermentation.

Biehl, B., Brunner E., Passern, D., Quesnel, V. C. and Adomako, D. J. Sci. Food Agric. 36 583–598 (1985). Acidification, Proteolysis and Flavour Potential in Fermenting Cocoa Beans.

Catty., D. and Raykundalia, C. Production and Quality control of Polyclonal Antibodies in: "Antibodies: A Practical Approach" Vol I, IRL Press (1988)

Cuming, A. C., Williams, R. S., and Cullimore, J. V. in "Immunology in Plant Science", Ed. Wang, T. L., Cambridge University Press, 1986. The use of Antibodies in Molecular Biology.

Dretzen, G., Bellard, M., Sassone-Corsi, P., and Chambon, P. Analytical Biochemistry 112, 295–298 (1981). A reliable method for the recovery of DNA fragments from agarose and acrylamide gels.

Eschenfeldt, W. H., Puskas, R. S., and Berger, S. L. Methods in Enzymology 152, 337–342 (1987). Homopolymeric Tailing.

Fritz et al (J. Food Sci. 50 946–950 (1985))

Gubler, U., and Hoffman, B. J. Gene 25, 263 (1983). A simple and very efficient method for generating cDNA libraries.

Hall, T. C., Ma, Y., Buchbinder, B. U., Pyrne J. W., Sun, S. M., and Bliss, F. A. Proc. Natl. Acad. Sci. USA 75, 3196–3200 (1978). Messenger RNA for G1 protein of French bean seeds: cell-free translation and product characterisation.

Hill, S. A. "Methods in Plant Virology", Blackwell 1984.

Johnston, J. R. in "Yeast: A practical approach". Eds Campbell, I., and Duffus, J. H. IRL Press, 1988. Yeast Genetics, Molecular Aspects.

Joubert, F. J, Henssen, C. and Dowdle, E. B. D. J. Biol. chem. 260, 12948–12953 (1985) The complete amino acid sequence of trypsin inhibitor DE-3 from Erythrina latissima seeds.

Koide, T. and Ikenaka, T. Eur. J. Biochem. 32, 417–431 (1973b). Amino-acid sequence of the carboxyl-terminal region and the complete amino-acid sequence of the soybean trypsin inhibitor (Kunitz).

Kreil, G. Annual Rev. Biochem. 50, 317–348 (1981). Transfer of proteins across membranes.

Laemmli, U. K. Nature 227, 680 (1970). Cleavage of structural proteins during the assembly of the head of bacteriophage T4.

Lipman, D. J., and Pearson, W. R. Science 227, 1435–1441 (1985). Rapid protein sequence similarity searches.

Maeda, K. Biochim. Biophys. Acta 871, 250–256 (1986). The complete amino-acid sequence of the endogenous a-amylase inhibitor in wheat.

Maniatis, T., Fritsch, E. F., and Sambrook, J. "Molecular Cloning: A Laboratory Manual", Cold Spring Harbour Laboratory, 1982.

Mason, P. J., and Williams, J. G. in "Nucleic Acid Hybridisation: A Practical Approach". Ed. Hames, B. D., and Higgins, S. J. IRL Press 1985. Hybridisation in the Analysis of Recombinant DNA.

Meinkoth, J., and Wahl, G. M. Analytical Biochemistry 138, 267 (1984). Methods of Southern blotting and DNA probing.

Miller, H. Methods in Enzymology 152, 145–170 (1987). Practical Aspects of Preparing Phage and Plasmid DNA: Growth, Maintenance and Storage of Bacteria and Bacteriophage.

Norrander, J., Kempe, T., and Messing, J. Gene 26, 101 (1983). Construction of improved M13 vectors using oligodeoxynucleotide-directed mutagensis.

Pettipher, G. L. Cafe Cacao The XXXIV 23–26 (1990). The Extraction and Partial Purification of Cocoa Storage Proteins.

Proudfoot, N. J., and Brownlee, G. G. Nature 263, 211–214 (1976). 3' Non-coding region sequences in enkayotic messenger RNA.

Roberts, B. E., and Paterson, B. M. Proc. Natl. Acad. Sci. USA 70, 2330 (1973). Efficient translation of tobacco mosaic virus RNA and rabbit globin 9S RNA in a cell-free system from commercial wheat gem.

Sanger, F., Nickden, S., and Coulson, A. R. Proc. Natl. Acad. Sci. USA 74, 5463–5467 (1977). DNA sequencing with chain-terminating inhibitors.

Schauder, B., Blocker, H., Frank, R., and McCarthy, J. E. G. Gene 52, 279–283 (1987). Inducible expression vectors incorporating the E. coli aptE translation initiation region.

Scott, R., Draper, J., Jefferson, R., Dury, G., and Jacob, L. in "Plant Genetic Transformation and Gene Expression: A Laboratory Manual". Eds. Draper, J., Scott, R., Armitage, P., Walden, R. Blackwell 1988. Analysis of gene organisation and expression in plants.

Shibata, H., Hara, S. and Ikenaka, T. J. Biochem. (Tokyo) 104, 537–543 (1988). Amino-acid sequence of winged bean (Psophocarpus tetragonolobus) chymotrypsin inhibitor, WCI-3.

Staden, R. Nucleic Acids Res. 14, 217–231 (1986). The current status and portability of our sequence .handling software.

Sudbery, P. E., Gleeson, M. A., Veale, R. A., Lederboer, A. M., and Zoetmulder, M. C. M. Biocem. Soc. Trans 16 1081–103 (1988). Hansenula polymorpha as a novel yeast system for the expression of heterologous genes.

Svendsen, L, Hejgaard, J. and Mundy, J. Carlsberg. Res. Commun. 51, 43–50 (1986). Complete amino-acid sequence of the α-amylase/subtilisin inhibitor from barley.

Taylor, J. W., Ott, J., and Eckstein, F. Nucleic Acids Res. 13, 8765–8785 (1985). The rapid generation of oligonucleotide-directed mutations at high frequency using phosphorothioate-modified DNA.

Towbin, H., Staehelin, T., and Gordon, J. *Proc. Natl. Acad. Sci. USA* 76, 4350–4534 (1979). Electrophoretic transfer of proteins from polyacrylamide gels to nitrocellulose sheets: procedure and some applications.

Von Heije, G. *Eur. Y. Biochem* 133, 17–21 (1983). Patterns of Amino-acids near Signal-Sequence Cleavage Sites.

Wahl, G. M., and Berger, S. L. *Methods in Enzymology* 152, 415–423 (1987). Screening Colonies or Plaques with Radioactive Nucleic Acid Probes.

Woods, D. E. *Focus* (Bethesda Research Labs) 6, 3 (1984). Oligonucleotide Screening of cDNA Libraries.

Woods, D. E., Markham, A. F., Rickel A. T., Goldberger, G., and Colten, H. R. *Proc. Natl. Acad. Sci. USA* 79, 5561 (1982).

Yamamoto, M., Hara, S. and Ikenaka, T. *J. Biochem.* (Tokyo) 94, 849–863 (1983). Amino-acid sequences of two trypsin inhibitors from winged bean seeds (*Psophocarpus tetragonolobus*).

---

We claim:

1. A purified and isolated 23 kD protein of *Theobroma cacao*, having the amino acid sequence shown in FIG. 2 (SEQ ID NO: 2).

2. A protein as claimed in claim 1, which is recombinant.

3. Recombinant or isolated nucleic acid coding for a protein as claimed in claim 1.

4. Nucleic acid as claimed in claim 3 which is DNA.

5. Nucleic acid as claimed in claim 4 having at least part of the sequence shown in FIG. 2 (SEQ ID NO: 1).

6. Nucleic acid as claimed in claim 3, which is in the form of a vector.

7. Nucleic acid as claimed in claim 6, wherein the vector is an expression vector and the protein-coding sequence is operably linked to a promoter.

8. Nucleic acid as claimed in claim 7, wherein the expression vector is a yeast expression vector and the promoter is a yeast pyruvate kinase (PK) promoter.

9. Nucleic acid as claimed in claim 7, wherein the expression vector is a bacterial expression vector and the promoter is a strong lambda promoter.

10. Nucleic acid as claimed in claim 7, further comprising a signal sequence having the amino acid sequence shown in FIG. 6B (SEQ ID NO: 19).

11. A host cell comprising nucleic acid as claimed in claim 6.

12. A host cell as claimed in claim 11 which is *Saccharomyces cerevisiae*.

13. A host cell as claimed in claim 11 which is *E. coli*.

* * * * *